US011085934B2

(12) United States Patent
Pollard et al.

(10) Patent No.: US 11,085,934 B2
(45) Date of Patent: Aug. 10, 2021

(54) BIOMARKERS FOR DIAGNOSING POST TRAUMATIC STRESS DISORDER

(71) Applicant: The Henry M. Jackson Foundation for the Advancement of Military Medicine, Inc., Bethesda, MD (US)

(72) Inventors: Harvey B. Pollard, Potomac, MD (US); Clifton L. Dalgard, Chevy Chase, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 0 days.

(21) Appl. No.: 15/759,507

(22) PCT Filed: Oct. 6, 2016

(86) PCT No.: PCT/US2016/055675
§ 371 (c)(1),
(2) Date: Mar. 12, 2018

(87) PCT Pub. No.: WO2017/062568
PCT Pub. Date: Apr. 13, 2017

(65) Prior Publication Data
US 2019/0113526 A1    Apr. 18, 2019

Related U.S. Application Data

(60) Provisional application No. 62/239,004, filed on Oct. 8, 2015.

(51) Int. Cl.
| | |
|---|---|
| *G01N 33/68* | (2006.01) |
| *A61K 31/15* | (2006.01) |
| *A61K 31/135* | (2006.01) |
| *A61K 31/4406* | (2006.01) |
| *A61K 31/454* | (2006.01) |
| *A61K 45/06* | (2006.01) |
| *A61K 31/4525* | (2006.01) |
| *A61K 31/343* | (2006.01) |
| *A61K 31/138* | (2006.01) |

(52) U.S. Cl.
CPC ....... *G01N 33/6896* (2013.01); *A61K 31/135* (2013.01); *A61K 31/138* (2013.01); *A61K 31/15* (2013.01); *A61K 31/343* (2013.01); *A61K 31/4406* (2013.01); *A61K 31/454* (2013.01); *A61K 31/4525* (2013.01); *A61K 45/06* (2013.01); *G01N 33/68* (2013.01); *G01N 33/6893* (2013.01); *G01N 2333/521* (2013.01); *G01N 2800/30* (2013.01)

(58) Field of Classification Search
CPC ......... G01N 33/6896; G01N 2333/521; G01N 2800/30; A61P 25/24
See application file for complete search history.

(56) References Cited

U.S. PATENT DOCUMENTS

| | | |
|---|---|---|
| 2014/0220019 A1 | 8/2014 | Ghayur et al. |
| 2015/0259740 A1 | 9/2015 | Pollard et al. |

FOREIGN PATENT DOCUMENTS

WO    2016/057775 A1    4/2016

OTHER PUBLICATIONS

Pollard, "Uncovering Novel Biomarkers for Early Diagnosis of Post Traumatic Stress Disorder (PTSD)"; Webpage [online]. Feb. 26, 2014 [retrieved on Jan. 24, 2017] Retrieved from the Internet: <URL: http://cdmrp.army.mil/phtbi/research_highlights/15pollard_highlight>; 1st-2nd paragraph.
(thermofisher.com) Safety Data Sheet. Webpage [online]. Apr. 30, 2014 [Retrieved on Jan. 25, 2017]. Retrieved from the Internet: <URL: https://tools.thermofisher.com/content/sfs/msds/2015/RF8937_MTR-NARF_EN.pdf>; p. 1; 1st paragraph.
(invitrogen.com) TARC/CCL 17 ABfinity™ Recombinant Rabbit Monoclonal Antibody—Purified. Webpage [online]. Jan. 10, 2011 [Retrieved on Jan. 25, 2017]. Retrieved from the Internet: <URL: https://tools.thermofisher.com/content/sfs/manuals/700655_rb_x_TARC_mab.pdf> p. 1, 1st column.
(ebioscience.com) AntiHuman CCL4 (MIP1beta); Webpage [online]. Apr. 2, 2015 [Retrieved on Jan. 25, 2017] Retrieved from the Internet: <URL: http://www.ebioscience.com/human-c,cl4-antibody-apc-fl34z31.htm>. p. 1, 1st paragraph.
International Search Report issued in corresponding International Patent Application No. PCT/US2016/055675.

*Primary Examiner* — Olga N Chernyshev
(74) *Attorney, Agent, or Firm* — MH2 Technology Law Group, LLP

(57) ABSTRACT

The invention relates to methods of determining if a subject is at risk of developing post-traumatic stress disorder (PTSD).

7 Claims, 20 Drawing Sheets
Specification includes a Sequence Listing.

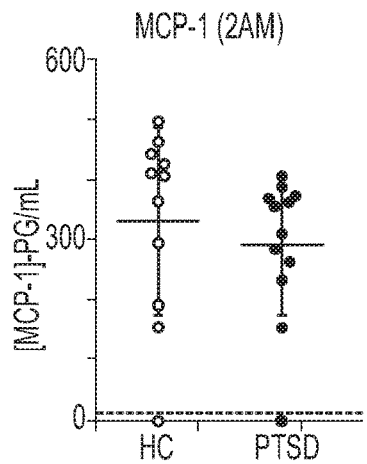
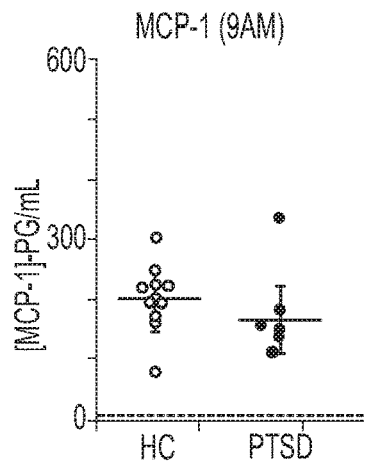
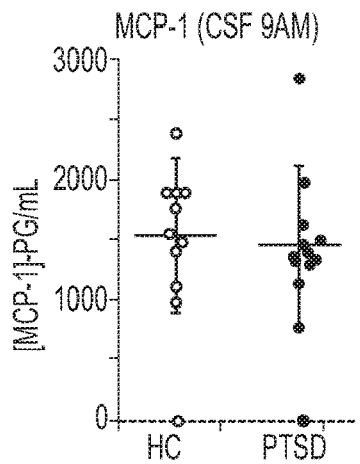
FIG. 1A  FIG. 1B  FIG. 1C
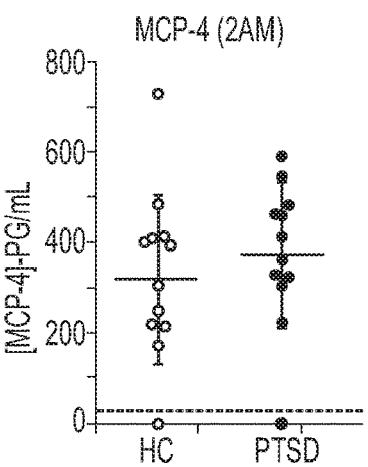
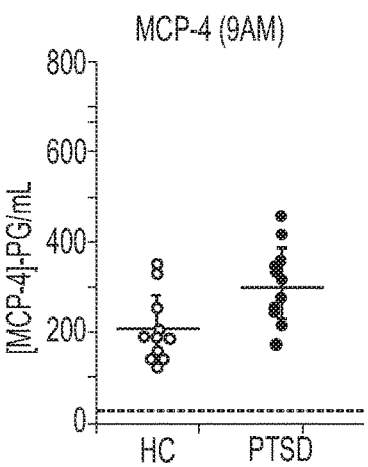
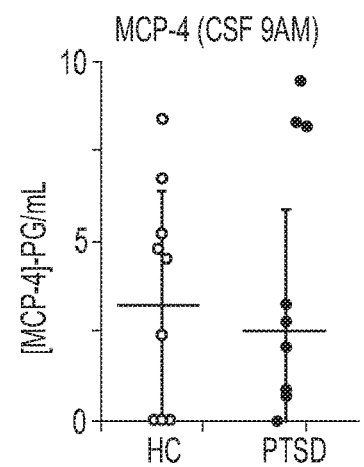
FIG. 1D  FIG. 1E  FIG. 1F
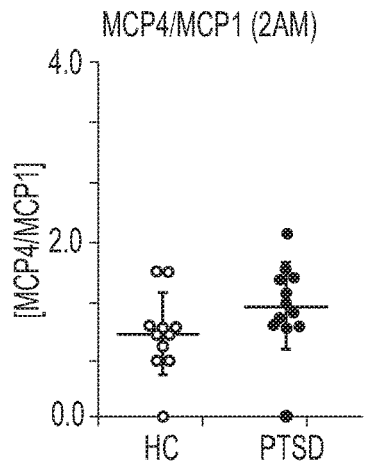
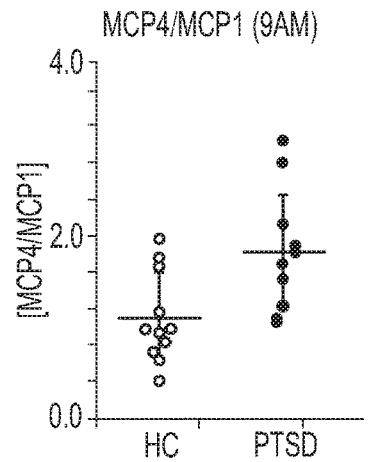
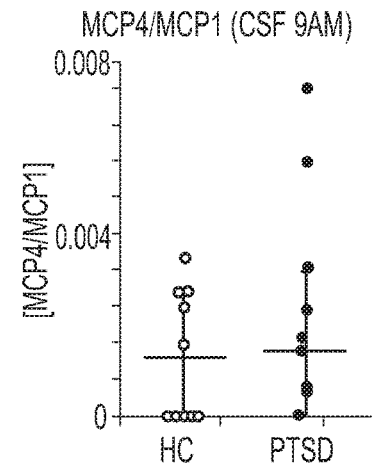
FIG. 1G  FIG. 1H  FIG. 1I

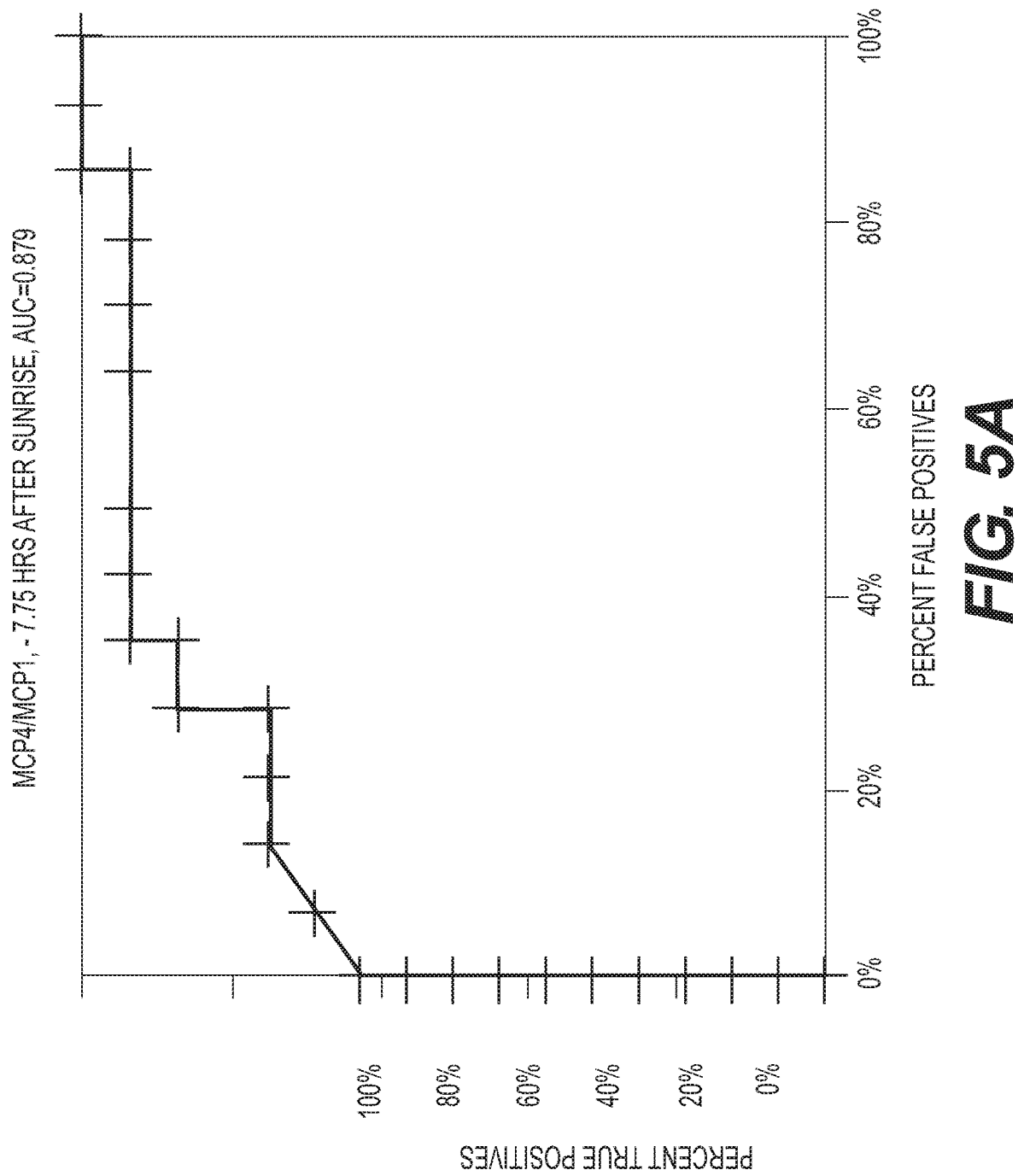

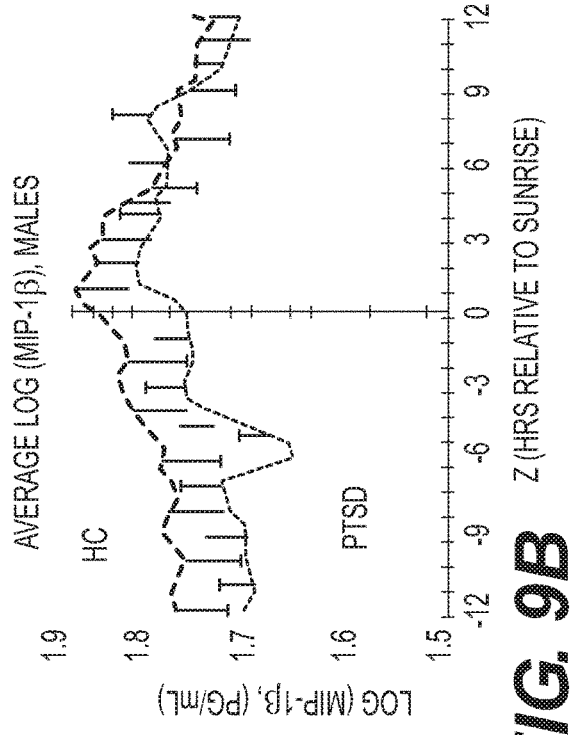
FIG. 9B
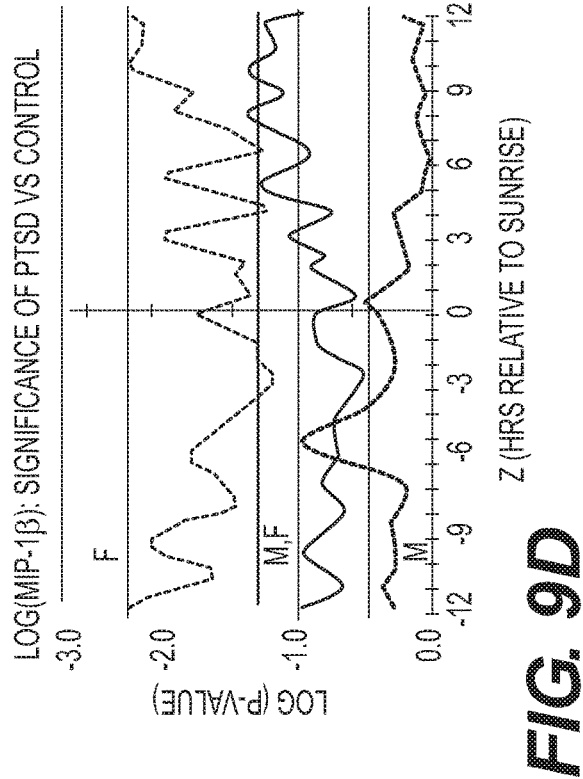
FIG. 9D
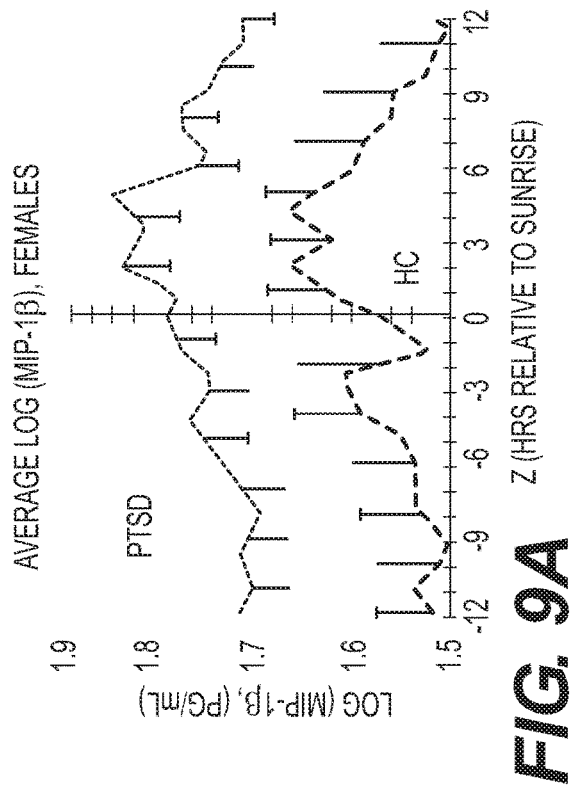
FIG. 9A
FIG. 9C

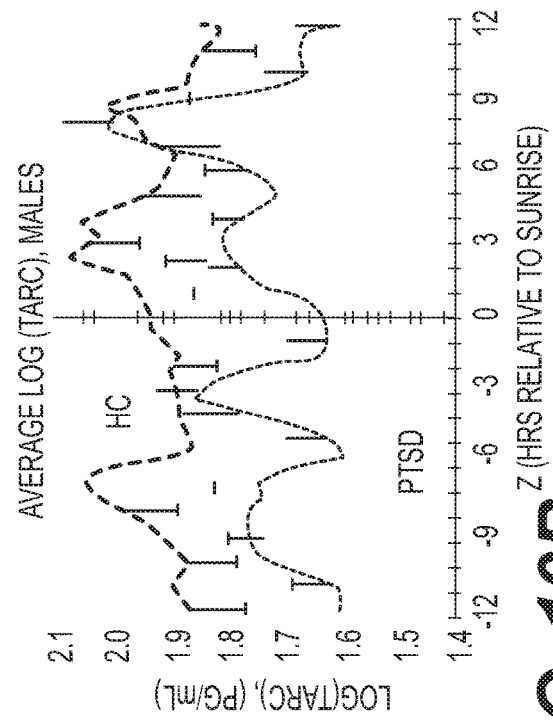
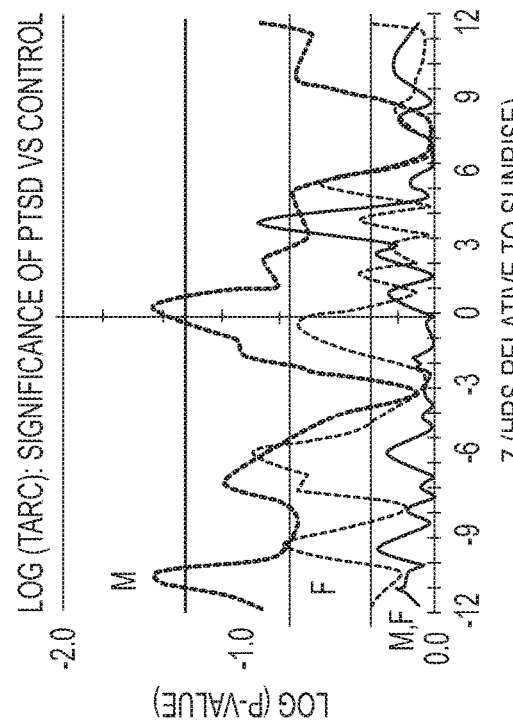
FIG. 10B
FIG. 10D
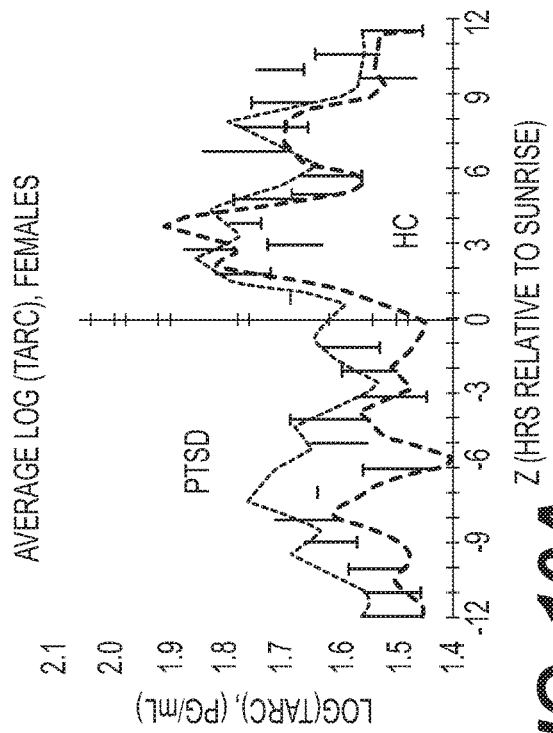
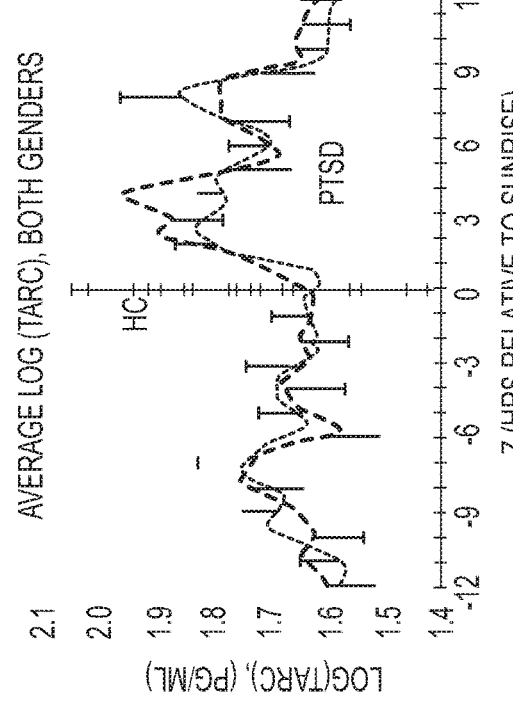
FIG. 10A
FIG. 10C

BIOMARKERS FOR DIAGNOSING POST TRAUMATIC STRESS DISORDER

This invention was made with government support under CDMRP-PTSD (PTO74415) issued by the Department of Defense and under W81XWH-08-2-0201 issued by the United States Army Medical Research and Materiel Command. The government has certain rights in the invention.

STATEMENT REGARDING FEDERALLY SPONSORED RESEARCH OR DEVELOPMENT

Part of the work performed during development of this invention utilized U.S. Government funds through grant number CDMRP-PTSD (PTO74415). The U.S. Government has certain rights in this invention.

REFERENCE TO SEQUENCE LISTING

A computer readable text file, entitled "044508-5052-P1-SequenceListing.txt," created on or about Oct. 8, 2015 with a file size of about 8.7 kb contains the sequence listing for this application and is hereby incorporated by reference in its entirety.

BACKGROUND OF THE INVENTION

Field of the Invention

The invention relates to methods of determining if a subject is at risk of developing post-traumatic stress disorder (PTSD).

Background of the Invention

Post-traumatic stress disorder (PTSD) is a psychiatric disease, which occurs following exposure to traumatic events. PTSD may be acute or chronic, and can have a waxing and waning course of symptoms that can persist for months, years or decades [2,3]. Patients with chronic PTSD have changes in their immune systems which have been interpreted as due to sustained activation of the hypothalamic-pituitary-adrenal (HPA) axis, and resultant sympathoadrenal-medullary (SAM) stress [4-6],[7]. The difference between a chronic PTSD patient and a resilient healthy control is that for a stress experience that resolves normally, the initially high levels of norepinephrine from the adrenal medulla, via the SAM, are eventually reduced by transient elevation of cortisol from the HPA. However, some studies have found chronic PTSD patients to have intrinsically low levels of circulating cortisol. Failure of feedback inhibition has been conjectured to be a driver for excessive levels of cell-mediated and proinflammatory cytokine expression [8-10]. For example, cytokines such as TNF-alpha and IL-6 are known to cross the blood brain barrier and to regulate the immune response through stimulation of the HPA axis [10,11]. Consistently, it has been reported that IL-1-beta [12], TNF-alpha [13], and IL-6 [14,15] are elevated in the serum of PTSD patients. Furthermore, in the cerebrospinal fluid (CSF) of PTSD patients, both IL-6 [16] and norepinephrine [17] are reported to be higher in PTSD patients than in normal controls. The transition from a conventional high cortisol state to a low cortisol/high norepinephrine state has also been documented in a cohort of pediatric PTSD patients [16].

Patients with a diagnosis of PTSD often have co-morbid conditions such as major depressive disorder (MDD), as well as addiction to alcohol and other drugs [6,19]. Interestingly, while PTSD patients who are co-morbid with MDD have higher levels of serum IL-6 [20], those PTSD patients without co-morbid MDD have serum IL-6 levels that are identical to normal controls [20]. Furthermore, in a carefully controlled study of CSF from the NIMH cohort of civilian chronic PTSD patients, all with smaller dorsal hippocampus and relatively free from MDD, concentrations of Corticotrophin Releasing Factor (CRF), IL-6, BDNF, IGF-1 and Substance P were identical to levels in CSF from normal controls [1]. These results seem to suggest that cytokines or chemokines may not be involved in PTSD.

SUMMARY OF THE INVENTION

The invention relates to methods of determining if a subject is at risk of developing post-traumatic stress disorder (PTSD), with the methods comprising determining the ratio of monocyte chemoattractant protein 4 (MCP-4) to monocyte chemoattractant protein 1 (MCP-1) and comparing the MCP-4/MCP-1 ratio (MMR) to a normal MMR. An elevation in the MMR over normal ratios is indicative that the subject has an increased risk of suffering from PTSD.

The invention relates to methods of monitoring the progression of post-traumatic stress disorder (PTSD) in a subject, with the methods comprising determining the MMR in the subject on at least two different days and comparing the MMRs over time to determine if the subject's MMR is changing over time. An increase in the subject's MMR over time is indicative that the PTSD is progressing in the subject.

The invention relates to methods of diagnosing post-traumatic stress disorder (PTSD) in a subject, with the methods comprising determining the MMR in the subject and comparing the MMR to a normal MMR. An elevation in the MMR over a normal ratio is indicative that the subject has or is suffering from PTSD.

The invention also relates to methods of diagnosing PTSD in a male subject, with the methods comprising determining levels of at least one marker selected from the group consisting of monocyte chemoattractant protein 1 (MCP-1) and thymus and activation-regulated chemokine (TARC) in at least one sample obtained from the male subject, and comparing the MCP-1 or TARC levels in the at least one sample to normal MCP-1 or TARC levels to determine if the male subject's MCP-1 or TARC levels are altered compared to the normal MCP-1 or TARC levels. A change in the male subject's MCP-1 or TARC levels indicative that the male subject has an increased risk of suffering from PTSD.

The invention also relates to methods of diagnosing PTSD is a female subject, with the methods comprising determining levels of at least one marker selected from the group consisting of monocyte chemoattractant protein 4 (MCP-4) and monocyte interacting protein 1β (MIP-1β) in at least one sample obtained from the female subject, and comparing the MCP-4 or MIP-1β levels in the at least one sample to normal MCP-4 or MIP-1β levels to determine if the female subject's MCP-4 or MIP-1β levels are altered compared to the normal MCP-4 or MIP-1β levels. A change in the female subject's MCP-4 or MIP-1β levels indicative that the female subject has an increased risk of suffering from PTSD.

BRIEF DESCRIPTION OF THE DRAWINGS

FIG. 1 (A-I) depicts dot-plot distributions of MCP-4, MCP-1 and the MCP-4/MCP-1 ratio in PTSD and healthy control plasma at 2 AM (a) and 9 AM (b), and in CSF at 9 AM (c). (a,b,c). MCP-1 (Monocyte Chemoattractant Protein-1, CCL2) is lower in PTSD plasma. (d,e,f). MCP-4 (Monocyte Chemoattractant Protein-4, CCL13) is higher in PTSD plasma. Levels of MCP-4 are vanishingly low in the CSF and cannot be accurately measured. (g,h,i). MCP-4/MCP-1 ratio is elevated in the 2 AM PTSD plasma (about 20%, p=0.02) and in 9 AM PTSD plasma (about 66%, p=0.004). All p values are two-tailed. Dotted horizontal lines are lower limits of detection (LLOD).

FIG. 9 (A-D) depicts the distribution of MIP-1β in plasma over a circadian interval for patients with PTSD and healthy controls.

FIG. 10 (A-D) depicts the distribution of TARC in plasma over a circadian interval for patients with PTSD and healthy controls.

DETAILED DESCRIPTION OF THE INVENTION

Figure 2A:
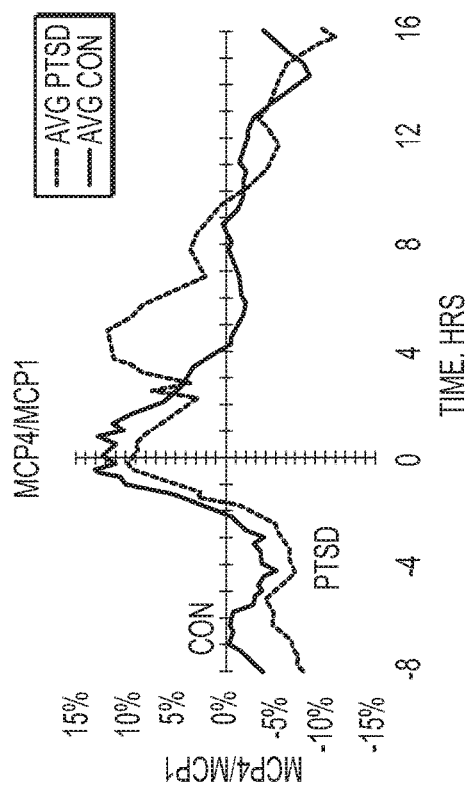
FIG. 2 (A-D) depicts the influence of PTSD on the circadian rhythms for the MCP-4/MCP-1 ratio, and individually for MCP-4 and MCP-1. (a). Circadian rhythm for the MCP-4/MCP-1 ratio in PTSD patients and healthy controls. The dotted contours are +/−2 standard deviations of the data at each time point. (b). Circadian rhythm data for the MCP-4/MCP-1 ratio in which the data have been normalized, patient by patient, and filtered for high frequency variation. (c). Circadian rhythm data for MCP-4 alone, in which the data have been normalized, patient by patient, and filtered for high frequency variation. (d). Circadian rhythm data for MCP-1 alone, in which the data have been normalized, patient by patient, and filtered for high frequency variation. PTSD seems to affect both the phase and the amplitude of the MCP-4/MCP-1 ratio, as well as its component analytes.

The invention relates to methods of determining if a subject is at risk of developing post-traumatic stress disorder (PTSD), with the methods comprising determining the ratio of monocyte chemoattractant protein 4 (MCP-4) to monocyte chemoattractant protein 1 (MCP-1) and comparing the MCP-4/MCP-1 ratio (MMR) a normal MMR. An elevation in the MMR over normal ratios is indicative that the subject has an increased risk of suffering from PTSD.

Both MCP-4(CCL13) and MCP-1(CCL2) share 67% sequence homology and function as molecular attractants ("chemokines") for monocytes, and, to a lesser extent, for lymphocytes and basophils. Both chemokines also share CCR2 as a common receptor [29,30]. Segman et al (2005) [31] studied peripheral blood mononuclear cells (PBMNs) in survivors of terror attacks in Israel. Yehuda et al (2009) [32] studied whole blood expression patterns in survivors of the World Trade Center attack in New York. Neylan et al (2011) [33] studied purified CD14+ monocytes, from men and women with PTSD, and other co-morbidities. In all three cases, a common observation was suppression of gene expression. The timing of blood collection was not mentioned or suggested in these publications.

The ratio of two monocyte chemokines, MCP-4 (CCL13) and MCP-1 (CCL2), constitute a time-independent, bivariate plasma biomarker for PTSD. Furthermore, in plasma from PTSD patients there is a disordered circadian pattern that is superimposed on the quantitatively elevated MCP-4/MCP-1 ratio, and its component individual analytes. These results suggest that the biomarker comprising the MCP-4/MCP-1 ratio is independent of an additional defect in circadian biology which may also characterize PTSD patients.

Recent studies, however, indicate that circulating monocytes exhibit a circadian oscillation, coinciding with endogenous MCP-1 expression that is driven by an autonomous circadian clock, and for which the time-dependent variation is independent of infection or metabolic stress [34,35]. In humans, nocturnal peak blood levels, encompassing the time period between 1 AM and 3 AM, can be observed for circulating monocytes, T lymphocytes and B lymphocytes [36]. Nocturnal monocytes activate the expression of MCP-1 [34]. Beginning at about 4 AM, levels of circulating monocytes, B cells and T cells begin to decline [36]. Coincidentally, monocyte expression of MCP-1 is blocked by the transcription factors CLOCK, BMAL1 and EZH2 [34]. MCP-1 plasma levels of healthy controls also significantly drop from 2 AM to 9 AM by about 70% (p=0.001) (Table 1 below and FIG. 1). In the case of PTSD patients, MCP-1 levels also drop, but by a greater proportion, about 90%, and with greater significance (p=$2 \times 10^{-6}$). This process is also seen in greater detail in the circadian pattern. It is therefore possible that this disease-specific difference is the dynamic basis for MCP-1 contributing to the lower denominator portion of the PTSD-specific MCP-4/MCP-1 biomarker.

TABLE 1

| | Healthy Controls | | | | PTSD patients | | | |
| Analyte | Ratio (CSF/plasma) | p-value | % R > 2 | % R < 0.5 | Ratio (CSF/plasma) | p-value | % R > 2 | % R < 0.5 |
| --- | --- | --- | --- | --- | --- | --- | --- | --- |
| GM-CSF | ~LLOD | n.a. | n.a. | n.a. | ~LLOD | n.a. | n.a. | n.a. |
| IFN-γ | ↑1.3 ± 0.4 | 0.406 | 44% | 22% | ≈0.9 ± 0.4 | 0.890 | 25% | 13% |
| IL-10 | ~LLOD | n.a | n.a | n.a | ~LLOD | n.a | n.a | n.a |
| IL-12 p70 | ~LLOD | 0.857 | 50% | 40% | ~LLOD | 0.703 | 20% | 40% |
| IL-1β | ~LLOD | n.a | n.a | n.a | ~LLOD | n.a | n.a | n.a |
| IL-2 | ↑2.4 ± 0.6 | 0.009 | 56% | 0% | ↑2.0 ± 0.8 | 0.098 | 44% | 22% |
| IL-6 | ↑1.6 ± 0.5 | 0.211 | 38% | 13% | ↑1.8 ± 0.4 | 0.020 | 45% | 0% |
| IL-8 | ↑20.4 ± 5.5 | 2E−06 | 100% | 0% | ↑17.7 ± 4.6 | 1E−06 | 100% | 0% |

TABLE 1-continued

|  | Healthy Controls | | | | PTSD patients | | | |
| --- | --- | --- | --- | --- | --- | --- | --- | --- |
| Analyte | Ratio (CSF/plasma) | p-value | % R > 2 | % R < 0.5 | Ratio (CSF/plasma) | p-value | % R > 2 | % R < 0.5 |
| TNF-α | ~LLOD | n.a. | n.a. | n.a. | ~LLOD | n.a. | n.a. | n.a. |
| Eotaxin-1 | ~LLOD | n.a. | n.a. | n.a. | ~LLOD | n.a. | n.a. | n.a. |
| Eotaxin-3 | ≈1.1 ± 0.1 | 0.649 | 0% | 0% | ≈0.9 ± 0.1 | 0.397 | 0%. | 9% |
| IP-10 | ↑3.6 ± 1.1 | 0.001 | 90% | 10% | ↑2.6 ± 1.0 | 0.024 | 73% | 9% |
| MCP-1 | ↑9.0 ± 1.3 | 2E−07 | 100% | 0% | ↑9.5 ± 1.3 | 4E−8 | 100% | 0% |
| MCP-4 | ~LLOD | n.a. | n.a. | n.a. | ~LLOD | n.a. | n.a. | n.a. |
| MDC | ↓18.6 ± 5.6 | 1E−04 | 0% | 100% | ↓11.6 ± 3.1 | 5E−04 | 0% | 100% |
| MIP-1β | ↑5.1 ± 1.0 | 1E−05 | 90% | 0% | ↑3.8 ± 0.9 | 2E−04 | 82% | 0% |
| TARC | ↓10.1 ± 8.6 | 0.030 | 0% | 67% | ↓4.7 ± 2.6 | 0.018 | 11% | 67% |
| plasma MCP-1 vs CSF IL-6 | ↑7.5 ± 1.9 | 4E−04 | 100% | 0% | ↑11.1 ± 3.9 | 5E−05 | 100% | 0% |

↑PTSD > HC;
↓PTSD < HC
~LLOD: (viz, the analyte was too low in either the or 9 AM plasma or 9 AM CSF to calculate accurately.
n.a.: not available Less is known about the genetics or possible circadian variation of plasma MCP-4. MCP-4 plasma levels, however, also significantly decrease from 2 AM to 9 AM, by about 60% in Healthy Controls (P=0.004)), compared to a significant decrease of only about 40% in PTSD patients (p=0.01). This process is also seen in greater detail in the circadian pattern (see FIG. 2c). Thus the PTSD patients appear to express relatively reduced amounts of both MCP-1 and MCP-4 as the wake period begins, with a greater reduction in MCP-1 than for MCP-4. Thus the elevation of the MCP-4/MCP-1 ratio in PTSD patients may be due to PTSD-dependent modifications in synthesis rates of both of these analytes.

Sleep disturbance is a hallmark feature of PTSD [21,22]. It is therefore possible that sleep deprivation might be the root cause of the disordered circadian profile for MCP-4 and MCP-1. In a comprehensive study of ten fully instrumented normal males, however, Born et al (1997) [36] reported that following a 24 hour sleep deprivation experience, the succeeding 24 hours were characterized only by a blunting of the circadian changes in immune cell numbers, including monocytes, as well as in TNFα, IL-1β, and IL-6 levels. Born et al also reported that there were no changes in phase or appearance of multimodality. Thus the circadianopathy observed for PTSD patients for plasma MCP-4 and MCP-1 appears to be disease-specific. Furthermore, because there were no observed PTSD-specific variations at the one available time point in any of the cytokines and chemokines in the CSF, the data disclosed herein may argue for a PTSD contribution to specific deficits in monocyte or immune cell biology. This conclusion is consistent with results mentioned above for PBMC [31] and whole blood [32], respectively, and for CD14+ mononuclear cells [33].

The central clock mechanism in the brain is run by light exposure and activation of CLOCK/BMAL1 signaling in the suprachiasmatic nucleus [37]. Subsidiary clocks in the periphery take their cue from this central mechanism, via the hypothalamic-Pituitary-Adrenal (HPA) axis, and adapt the exact subsidiary timing to their own requirements. In healthy controls, the circadian clock program is intrinsically plastic and can reversibly changed in response to alterations in, for example, metabolism or sunrise time[28]. By contrast, chronic neuropsychiatric disorders have been associated with conditions in which the central clock appears to permanently "lose track of time" [38]. In the case of PTSD, however, these patients exhibit phase-shifted peripheral clocks for MCP-1 and MCP-4 and, at least in the case of MCP-4, a different pattern altogether.

Figure 2B:
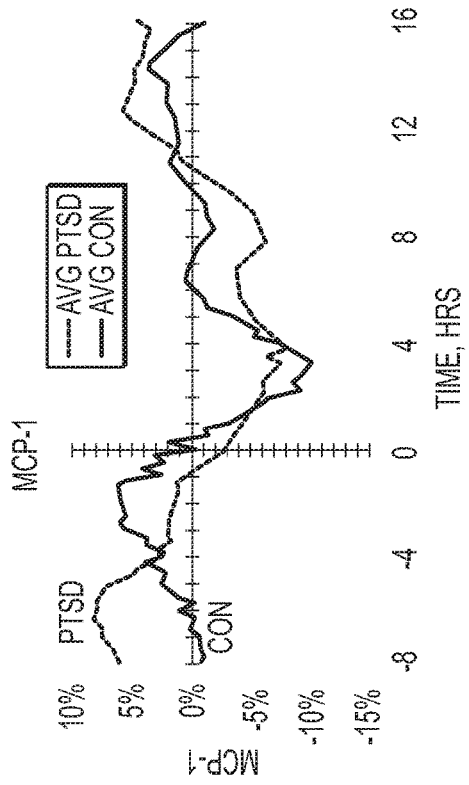
Figure 2C:
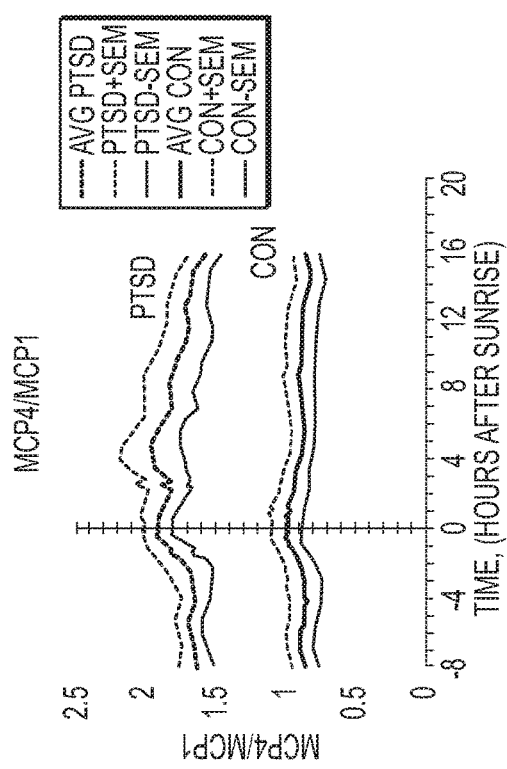
Figure 2D:
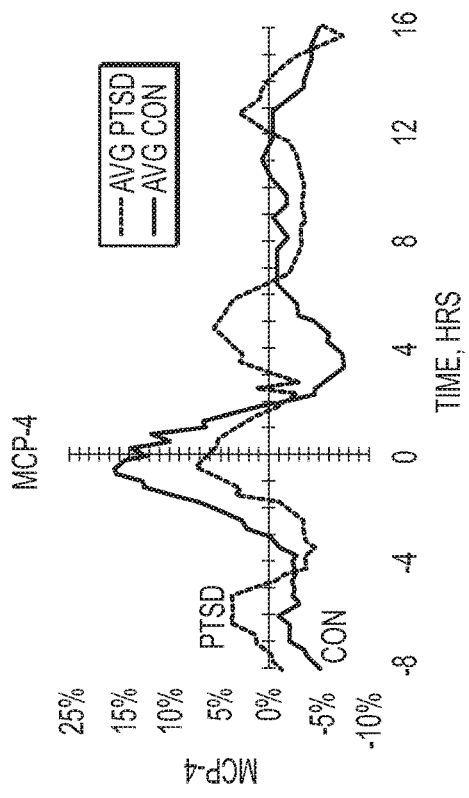

For example, FIG. 2c shows that MCP-4 levels in healthy controls have a monomodal distribution over 24 hours. In contrast MCP-4 distribution in PTSD patients transitions to four discrete peaks over 24 hours. In the case of MCP-1, FIG. 2d shows MCP-1 in healthy controls also distributes in a monomodel distribution, peaking in the late night hours and lagging MCP-4 by about 2 hours (see FIG. 3). MCP-1 in PTSD patients, however, lags the major late night peak by about 6 hours, and appears to "catch up" somewhat to lower levels in the late afternoon and evening.

Data presented here show that few PTSD-specific changes in CSF can be detected from simply screening cytokines and chemokines at 9 AM. In fact, the only detectable change was a small reduction in IL-8. These data are consistent with data reported by Bonne et al (2011) for a subset of cytokines in the same CSF samples.

In the meantime, there are other concentration gradients between 9 AM CSF and plasma. The highest elevation in the gradients was for IL-8 (elevated about 14-fold); for MCP-1 (elevated about 7-fold); for IP-10 (elevated about 7-fold); for MIP-1β and for Eotaxin 3 (both elevated about 4-fold). The most reduced analytes were MCP-4 (reduced about 80-100-fold); Eotaxin 1 (reduced about 18-fold); MDC (reduced about 25-fold); TARC (reduced about 9-fold); and TNFα (reduced about 6-fold).

Based on the data herein, the MCP-4/MCP-1 ratio constitutes a quantitative candidate biomarker for PTSD, which has the benefit of being measurable at any hour blood can be drawn. Furthermore, the circadian pattern of expression for both the ratio, and its individual components, MCP-4 and MCP-1, are phase-shifted and multimodal compared to healthy controls. Thus, the relative MCP-4 and MCP-1 levels in plasma, accessed through the MCP-4/MCP-1 ratio, can be used as a functional biomarker for PTSD. Moreover, these data suggest that the MCP-4/MCP-1 ratio is independent of any defect in circadian biology which could also affect PTSD patients.

In addition, the circadian rhythms for plasma MCP-4 and MCP-1 are disordered in PTSD patients. Thus it cannot be ruled out that circadian dysfunction, possibly involving monocytes, or immune cells in general, may play an important role in the behavioral problems afflicting this class of psychiatric patients.

The invention also relates to methods of diagnosing PTSD in a male subject, with the methods comprising determining levels of at least one marker selected from the group consisting of monocyte chemoattractant protein 1 (MCP-1) and thymus and activation-regulated chemokine (TARC) in at least one sample obtained from the male subject, and comparing the MCP-1 or TARC levels in the at least one sample to normal MCP-1 or TARC levels to determine if the male subject's MCP-1 or TARC levels are altered compared to the normal MCP-1 or TARC levels. A change in the male subject's MCP-1 or TARC levels indicative that the male subject has an increased risk of suffering from PTSD.

MCP-1 or CCL2, UniProt Accession No. P13500, is a well-known C—C motif chemokine and is tethered to endothelial cells via proteoglycans. MCP-1 is a protein of 99 amino acids, with residues 1-23 being the signal sequence. MCP-1 typically binds to the CCR2 and CCR4 receptors. As used herein, the term MCP-1 is not limited to a specific amino acid sequence but instead is used to mean a chemokine found in the blood of a subject that would be readily characterized as MCP-1 in any standard or commercially available analysis, e.g., ELISA assay. Thus any proteins detected as MCP-1, e.g., ability to bind to an antibody raised against a known MCP-1 protein, would be considered MCP-1 for the purposes of the present invention. In some embodiments, the term MCP-1 means the mature (full length polypeptide without the signal sequence) form of the MCP-1 protein.

In specific embodiments, the term MCP-1 means a protein with an amino acid sequence at least about 75%, 80%, 85%, 86%, 87%, 88%, 89%, 90%, 91%, 92%, 93%, 94%, 95%, 96%, 97%, 98%, 99% or 100% identical to the amino acid sequence of SEQ ID NO:1. In other embodiments, the term MCP-1 means a protein with an amino acid sequence at least about 75%, 80%, 85%, 86%, 87%, 88%, 89%, 90%, 91%, 92%, 93%, 94%, 95%, 96%, 97%, 98%, 99% or 100% identical to the amino acid sequence of SEQ ID NO:2.

```
                                              (SEQ ID NO: 1)
MKVSAALLCL LLIAATFIPQ GLAQPDAINA PVTCCYNFTN
RKISVQRLAS YRRITSSKCP KEAVIFKTIV AKEICADPKQ
KWVQDSMDHL DKQTQTPKT (SEQ ID NO: 2)
QPDAINAPVT CCYNFTNRKI SVQRLASYRR ITSSKCPKEA
VIFKTIVAKE ICADPKQKWV QDSMDHLDKQ TQTPKT
```

Thymus and activation-regulated chemokine (TARC or CCL17), UniProt Accession No. Q92583, is a well-known C—C motif chemokine that is generally expressed in the thymus and, to lesser extent, in the lungs, colon and small intestine. TARC is a protein of 94 amino acids, with residues 1-23 constituting the signal sequence. It generally acts as a chemotactic factor for T cells and may also participate in T cell development as well as trafficking of mature T cells. TARC typically binds to the CCR4 receptor. As used herein, the term TARC is not limited to a specific amino acid sequence but instead is used to mean a chemokine found in the blood of a subject that would be readily characterized as TARC in any standard or commercially available analysis, e.g., ELISA assay. For example, TARC has at least two naturally occurring variants at amino acid positions 5 and 67 of the full length peptide chain. Both variants, however, are detected as TARC in ELISA assays, thus both variants would be considered as TARC for the purposes of the present invention. Any proteins detected as TARC, e.g., ability to bind to an antibody raised against a known TARC protein, would be considered TARC for the purposes of the present invention. In some embodiments, the term TARC means the mature (full length polypeptide without the signal sequence) form of the TARC protein.

In specific embodiments, the term TARC means a protein with an amino acid sequence at least about 75%, 80%, 85%, 86%, 87%, 88%, 89%, 90%, 91%, 92%, 93%, 94%, 95%, 96%, 97%, 98%, 99% or 100% identical to the amino acid sequence of SEQ ID NO:3. In other embodiments, the term TARC means a protein with an amino acid sequence at least about 75%, 80%, 85%, 86%, 87%, 88%, 89%, 90%, 91%, 92%, 93%, 94%, 95%, 96%, 97%, 98%, 99% or 100% identical to the amino acid sequence of SEQ ID NO:4.

```
                                              (SEQ ID NO: 3)
MAPLKMLALV TLLLGASLQH IHAARGTNVG RECCLEYFKG
AIPLRKLKTW YQTSEDCSRD AIVFVTVQGR AICSDPNNKR
VKNAVKYLQS LERS (SEQ ID NO: 4)
ARGTNVGREC CLEYFKGAIP LRKLKTWYQT SEDCSRDAIV
FVTVQGRAIC SDPNNKRVKN AVKYLQSLER S
```

The invention also relates to methods of diagnosing PTSD is a female subject, with the methods comprising determining levels of at least one marker selected from the group consisting of monocyte chemoattractant protein 4 (MCP-4) and monocyte interacting protein 1β (MIP-1β) in at least one sample obtained from the female subject, and comparing the MCP-4 or MIP-1β levels in the at least one sample to normal MCP-4 or MIP-1β levels to determine if the female subject's MCP-4 or MIP-1β levels are altered compared to the normal MCP-4 or MIP-1β levels. A change in the female subject's MCP-4 or MIP-1β levels indicative that the female subject has an increased risk of suffering from PTSD.

Monocyte interacting protein 1β (MIP-1β) is a chemokine that is generated from the CCL4 C—C motif chemokine. Specifically, the CCL4 chemokine is a protein of 92 amino acids, with residues 1-23 being the signal sequence. The "mature" CCL4 protein is thus a protein of 69 residues with the amino acid sequence of residues 24-92 of the full length CCL4. MIP-1β is further processed to a slightly short chain constituting residues 3-69 of the mature CCL4 protein (residues 26-92 of the full length CCL4). As used herein, MP-1β can include the full length and mature forms of CCL4, as well as the short form of CCL4. In specific embodiments, the term MIP-1β means only the mature CCL4 chain and the shorter CCL4 chain (residues 3-69 of the mature CCL4) version of the protein. In other specific embodiments, the term MIP-1β means only the short chain (residues 3-69 of the mature CCL4) version of the protein.

In specific embodiments, the term MIP-1β means a protein with an amino acid sequence at least about 75%, 80%, 85%, 86%, 87%, 88%, 89%, 90%, 91%, 92%, 93%, 94%, 95%, 96%, 97%, 98%, 99% or 100% identical to the amino acid sequence of SEQ ID NO:5 (full length). In other embodiments, the term MIP-1β means a protein with an amino acid sequence at least about 75%, 80%, 85%, 86%, 87%, 88%, 89%, 90%, 91%, 92%, 93%, 94%, 95%, 96%, 97%, 98%, 99% or 100% identical to the amino acid sequence of SEQ ID NO:6 (mature CCL4). In other embodiments, the term MIP-1β means a protein with an amino acid sequence at least about 75%, 80%, 85%, 86%, 87%, 88%, 89%, 90%, 91%, 92%, 93%, 94%, 95%, 96%, 97%, 98%, 99% or 100% identical to the amino acid sequence of SEQ ID NO:7 (MIP-1β).

```
                                    (SEQ ID NO: 5)
MKLCVTVLSL LMLVAAFCSP ALSAPMGSDP PTACCFSYTA
RKLPRNFVVD YYETSSLCSQ PAVVFQTKRS KQVCADPSES
WVQEYVYDLE LN (SEQ ID NO: 6)
APMGSDPPTA CCFSYTARKL PRNFVVDYYE TSSLCSQPAV
VFQTKRSKQV CADPSESWVQ EYVYDLELN (SEQ ID NO: 7)
MGSDPPTACC FSYTARKLPR NFVVDYYETS SLCSQPAVVF
QTKRSKQVCA DPSESWVQEY VYDLELN
```

MCP-4 or CCL 13, UniProt Accession No. Q99616, is a well-known C—C motif chemokine and is widely expressed in small intestine, thymus, colon, lung, trachea, stomach, lymph nodes and pulmonary artery smooth muscle cells. MCP-4 is a protein of 98 amino acids, with residues 1-16 being the signal sequence. The mature or "long chain" MCP-4 protein (full length protein without the signal sequence) can be further processed or cleaved into two additional chains, known as medium and short chains, which are shown below. MCP-4 typically binds to the CCR2B and CCR3 receptors and is a chemotactic factor that attracts monocytes, lymphocytes, basophils and eosinophils. As used herein, the term MCP-4 is not limited to a specific amino acid sequence but instead is used to mean a chemokine found in the blood of a subject that would be readily characterized as MCP-4 in any standard or commercially available analysis, e.g., ELISA assay. Thus any proteins detected as MCP-4, e.g., ability to bind to an antibody raised against a known MCP-4 protein, would be considered MCP-4 for the purposes of the present invention. In specific embodiments, the term MCP-4 means only the mature MCP-4 chain, the medium MCP-4 chain version and the shorter MCP-4 chain version of the protein. In other specific embodiments, the term MCP-4 means only the medium MCP-4 chain version and the shorter MCP-4 chain version of the protein. In additional embodiments, the term MCP-4 means only the shorter MCP-4 chain version of the protein.

In specific embodiments, the term MCP-4 means a protein with an amino acid sequence at least about 75%, 80%, 85%, 86%, 87%, 88%, 89%, 90%, 91%, 92%, 93%, 94%, 95%, 96%, 97%, 98%, 99% or 100% identical to the amino acid sequence of SEQ ID NO:8 (full length). In other embodiments, the term MCP-4 means a protein with an amino acid sequence at least about 75%, 80%, 85%, 86%, 87%, 88%, 89%, 90%, 91%, 92%, 93%, 94%, 95%, 96%, 97%, 98%, 99% or 100% identical to the amino acid sequence of SEQ ID NO:9 (long chain MCP-4). In other embodiments, the term MCP-4 means a protein with an amino acid sequence at least about 75%, 80%, 85%, 86%, 87%, 88%, 89%, 90%, 91%, 92%, 93%, 94%, 95%, 96%, 97%, 98%, 99% or 100% identical to the amino acid sequence of SEQ ID NO:10 (medium chain MCP-4). In other embodiments, the term MCP-4 means a protein with an amino acid sequence at least about 75%, 80%, 85%, 86%, 87%, 88%, 89%, 90%, 91%, 92%, 93%, 94%, 95%, 96%, 97%, 98%, 99% or 100% identical to the amino acid sequence of SEQ ID NO:11 (short chain MCP-4).

```
                                    (SEQ ID NO: 8)
MKVSAVLLCL LLMTAAFNPQ GLAQPDALNV PSTCCFTFSS
KKISLQRLKS YVITTSRCPQ KAVIFRTKLG KEICADPKEK
WVQNYMKHLG RKAHTLKT (SEQ ID NO: 9)
FNPQGLAQPD ALNVPSTCCF TFSSKKISLQ RLKSYVITTS
RCPQKAVIFR TKLGKEICAD PKEKWVQNYM KHLGRKAHTL
KT (SEQ ID NO: 10)
LAQPDALNVP STCCFTFSSK KISLQRLKSY VITTSRCPQK
AVIFRTKLGK EICADPKEKW VQNYMKHLGR KAHTLKT (SEQ ID NO: 11)
QPDALNVPST CCFTFSSKKI SLQRLKSYVI TTSRCPQKAV
IFRTKLGKEI CADPKEKWVQ NYMKHLGRKA HTLKT
```

A polypeptide having an amino acid sequence at least, for example, about 95% "identical" to a reference an amino acid sequence, e.g., SEQ ID NO:2, is understood to mean that the amino acid sequence of the polypeptide is identical to the reference sequence except that the amino acid sequence may include up to about five modifications per each 100 amino acids of the reference amino acid sequence. In other words, to obtain a peptide having an amino acid sequence at least about 95% identical to a reference amino acid sequence, up to about 5% of the amino acid residues of the reference sequence may be deleted or substituted with another amino acid or a number of amino acids up to about 5% of the total amino acids in the reference sequence may be inserted into the reference sequence. These modifications of the reference sequence may occur at the N-terminus or C-terminus positions of the reference amino acid sequence or anywhere between those terminal positions, interspersed either individually among amino acids in the reference sequence or in one or more contiguous groups within the reference sequence.

As used herein, "identity" is a measure of the identity of nucleotide sequences or amino acid sequences compared to a reference nucleotide or amino acid sequence. In general, the sequences are aligned so that the highest order match is obtained. "Identity" per se has an art-recognized meaning and can be calculated using published techniques. (See, e.g., Computational Molecular Biology, Lesk, A. M., ed., Oxford University Press, New York (1988); Biocomputing: Informatics And Genome Projects, Smith, D. W., ed., Academic Press, New York (1993); Computer Analysis of Sequence Data, Part I, Griffin, A. M., and Griffin, H. G., eds., Humana Press, New Jersey (1994); von Heinje, G., Sequence Analysis In Molecular Biology, Academic Press (1987); and Sequence Analysis Primer, Gribskov, M. and Devereux, J., eds., M Stockton Press, New York (1991)). While there are several methods to measure identity between two polynucleotide or polypeptide sequences, the term "identity" is well known to skilled artisans (Carillo, H. & Lipton, D., Siam J Applied Math 48:1073 (1988)). Methods commonly employed to determine identity or similarity between two sequences include, but are not limited to, those disclosed in Guide to Huge Computers, Martin J. Bishop, ed., Academic Press, San Diego (1994) and Carillo, H. & Lipton, D., Siam J Applied Math 48:1073 (1988). Computer programs may also contain methods and algorithms that calculate identity and similarity. Examples of computer program methods to determine identity and similarity between two sequences include, but are not limited to, GCG program package (Devereux, J., et al., Nucleic Acids Research 12(i):387 (1984)), BLASTP, ExPASy, BLASTN, FASTA (Atschul, S. F., et al., J Molec Biol 215:403 (1990)) and FASTDB. Examples of methods to determine identity and similarity are discussed in Michaels, G. and Garian, R., Current Protocols in Protein Science, Vol 1, John Wiley & Sons, Inc. (2000), which is incorporated by reference.

In one embodiment of the present invention, the algorithm used to determine identity between two or more polypeptides is BLASTP. In another embodiment of the present invention, the algorithm used to determine identity between two or more polypeptides is FASTDB, which is based upon the algorithm of Brutlag et al. (Comp. App. Biosci. 6:237-245 (1990), incorporated by reference). In a FASTDB sequence alignment, the query and reference sequences are amino sequences. The result of sequence alignment is in percent identity. In one embodiment, parameters that may be used in a FASTDB alignment of amino acid sequences to calculate percent identity include, but are not limited to: Matrix=PAM, k-tuple=2, Mismatch Penalty=1, Joining Penalty=20, Randomization Group Length=0, Cutoff Score=1, Gap Penalty=5, Gap Size Penalty 0.05, Window Size=500 or the length of the subject amino sequence, whichever is shorter.

If the reference sequence is shorter or longer than the query sequence because of N-terminus or C-terminus additions or deletions, but not because of internal additions or deletions, a manual correction can be made, because the FASTDB program does not account for N-terminus and C-terminus truncations or additions of the reference sequence when calculating percent identity. For query sequences truncated at the N- or C-termini, relative to the reference sequence, the percent identity is corrected by calculating the number of residues of the query sequence that are N- and C-terminus to the reference sequence that are not matched/aligned, as a percent of the total bases of the query sequence. The results of the FASTDB sequence alignment determine matching/alignment. The alignment percentage is then subtracted from the percent identity, calculated by the above FASTDB program using the specified parameters, to arrive at a final percent identity score. This corrected score can be used for the purposes of determining how alignments "correspond" to each other, as well as percentage identity. Residues of the reference sequence that extend past the N- or C-termini of the query sequence may be considered for the purposes of manually adjusting the percent identity score. That is, residues that are not matched/aligned with the N- or C-termini of the comparison sequence may be counted when manually adjusting the percent identity score or alignment numbering.

For example, a 90 amino acid residue query sequence is aligned with a 100 residue reference sequence to determine percent identity. The deletion occurs at the N-terminus of the query sequence and therefore, the FASTDB alignment does not show a match/alignment of the first 10 residues at the N-terminus. The 10 unpaired residues represent 10% of the reference sequence (number of residues at the N- and C-termini not matched/total number of residues in the reference sequence) so 10% is subtracted from the percent identity score calculated by the FASTDB program. If the remaining 90 residues were perfectly matched (100% alignment) the final percent identity would be 90% (100% alignment–10% unmatched overhang). In another example, a 90 residue query sequence is compared with a 100 reference sequence, except that the deletions are internal deletions. In this case the percent identity calculated by FASTDB is not manually corrected, since there are no residues at the N- or C-termini of the subject sequence that are not matched/aligned with the query. In still another example, a 110 amino acid query sequence is aligned with a 100 residue reference sequence to determine percent identity. The addition in the query occurs at the N-terminus of the query sequence and therefore, the FASTDB alignment may not show a match/alignment of the first 10 residues at the N-terminus. If the remaining 100 amino acid residues of the query sequence have 95% identity to the entire length of the reference sequence, the N-terminal addition of the query would be ignored and the percent identity of the query to the reference sequence would be 95%.

As used herein, the terms "correspond(s) to" and "corresponding to," as they relate to sequence alignment, are intended to mean enumerated positions within the reference protein, e.g., wild-type MCP-1, and those positions in a mutant or related MCP-1 that align with the positions on the reference protein. Thus, when the amino acid sequence of a subject peptide is aligned with the amino acid sequence of a reference MCP-1, e.g., SEQ ID NO:2, the amino acids in the subject sequence that "correspond to" certain enumerated positions of the reference sequence are those that align with these positions of the reference sequence, e.g., SEQ ID NO:2, but are not necessarily in these exact numerical positions of the reference sequence. Methods for aligning sequences for determining corresponding amino acids between sequences are described herein. Accordingly, embodiments of the present invention comprise detecting or determining levels (or ratios thereof) of biomarkers, with the biomarkers corresponding to MCP-1, MCP-4, TARC and/or MIP-1β.

As used herein, the term subject or "test subject" indicates a mammal, in particular a human or non-human primate. The test subject may or may not be in need of an assessment of a predisposition to PTSD. For example, the test subject may or may not have a recollection of an experience that could be associated with PTSD prior to applying the methods of the present invention. In another embodiment, the test subject has not been identified as a subject that may have had an experienced that could lead to PTSD prior to applying the methods of the present invention.

As used herein, PTSD is used as it is commonly understood in the art. In select embodiments, PTSD in the subject is assessed using the Structured Clinical Interview for DSM-IV (SCID) as is understood in the art. As is also understood in the art, the severity of PTSD can range from mild to severe. In select embodiments of the present invention, the severity of the PTSD can be assessed at any time, i.e., before or after determining the MMR in the subject. The severity of the PTSD can be assessed in any manner, such as, but not limited to, the Clinician-Administered PTSD scale (CAPS).

As used herein, the term means "increased risk" is used to mean that the test subject has an increased chance of developing or acquiring PTSD compared to a normal individual. The increased risk may be relative or absolute and may be expressed qualitatively or quantitatively. For example, an increased risk may be expressed as simply determining the subject's MMR, TARC levels and/or MIP-1β levels and placing the patient in an "increased risk" category, based upon previous population studies. Alternatively, a numerical expression of the subject's increased risk may be determined based upon the MMR, TARC levels and/or MIP-1β levels, respectively. As used herein, examples of expressions of an increased risk include but are not limited to, odds, probability, odds ratio, p-values, attributable risk, relative frequency, positive predictive value, negative predictive value, and relative risk.

For example, the correlation between a subject's MMR, TARC levels and/or MIP-1β levels and the likelihood of suffering from PTSD may be measured by an odds ratio (OR) and by the relative risk (RR). If $P(R^+)$ is the probability of developing PTSD for individuals with the risk profile (R) and $P(R^-)$ is the probability of developing PTSD for individuals without the risk profile, then the relative risk is the ratio of the two probabilities: $RR=P(R^+)/P(R^-)$.

In case-control studies, however, direct measures of the relative risk often cannot be obtained because of sampling design. The odds ratio allows for an approximation of the relative risk for low-incidence diseases and can be calculated: $OR=(F^+/(1-F^+))/(F^-/(1-F^-))$, where $F^+$ is the frequency of a risk profile in cases studies and $F^-$ is the frequency of risk profile in controls. $F^+$ and $F^-$ can be calculated using the MMR frequencies of the study.

The attributable risk (AR) can also be used to express an increased risk. The AR describes the proportion of individuals in a population exhibiting PTSD due to a specific member of the MMR or TARC levels and/or MIP-1β levels. AR may also be important in quantifying the role of individual components (specific member, e.g., MCP-4 or MCP-1) in condition etiology and in terms of the public health impact of the individual marker. The public health relevance of the AR measurement lies in estimating the proportion of cases of PTSD in the population that could be prevented if the MMR, TARC levels and/or MIP-1β levels or individual component were considered normal. AR may be determined as follows: $AR=P_E(RR-1)/(P_E(RR-1)+1)$, where AR is the risk attributable to an MMR, TARC levels and/or MIP-1β levels, and $P_E$ is the frequency of exposure to an MMR, TARC levels and/or MIP-1β levels within the population at large. RR is the relative risk, which can be approximated with the odds ratio when the MMR, TARC levels and/or MIP-1β levels under study has a relatively low incidence in the general population.

In one embodiment, the increased risk of a patient can be determined from p-values that are derived from association studies. Specifically, associations with specific MMRs, TARC levels and/or MIP-1β levels can be performed using regression analysis by regressing the MMR, TARC levels and/or MIP-1β levels with PTSD. In addition, the regression may or may not be corrected or adjusted for one or more factors. The factors for which the analyses may be adjusted include, but are not limited to age, sex, weight, ethnicity, geographic location, fasting state, state of pregnancy or post-pregnancy, menstrual cycle, general health of the subject, alcohol or drug consumption, caffeine or nicotine intake and circadian rhythms, and the subject's genotype to name a few.

Increased risk can also be determined from p-values that are derived using logistic regression. Binomial (or binary) logistic regression is a form of regression which is used when the dependent is a dichotomy and the independents are of any type. Logistic regression can be used to predict a dependent variable on the basis of continuous and/or categorical independents and to determine the percent of variance in the dependent variable explained by the independents; to rank the relative importance of independents; to assess interaction effects; and to understand the impact of covariate control variables. Logistic regression applies maximum likelihood estimation after transforming the dependent into a "logit" variable (the natural log of the odds of the dependent occurring or not). In this way, logistic regression estimates the probability of a certain event occurring. These analyses are conducted with the program SAS.

Techniques to assay levels of individual components of the MMR, TARC levels and/or MIP-1β levels from test samples are well known to the skilled technician, and the invention is not limited by the means by which the components are assessed. In one embodiment, levels of the individual components of the MMR, TARC levels and/or MIP-1β levels are assessed using mass spectrometry in conjunction with ultra-performance liquid chromatography (UPLC), high-performance liquid chromatography (HPLC), and UPLC to name a few. Other methods of assessing levels of the individual components include biological methods, such as but not limited to ELISA assays The assessment of the levels of the individual components of the MMR, TARC levels and/or MIP-1β levels can be expressed as absolute or relative values and may or may not be expressed in relation to another component, a standard an internal standard or another molecule of compound known to be in the sample. If the levels are assessed as relative to a standard or internal standard, the standard may be added to the test sample prior to, during or after sample processing.

The subject's MMR, TARC levels and/or MIP-1β levels is(are) compared to an MMR, TARC levels and/or MIP-1β levels that is(are) deemed to be a normal MMR, TARC levels and/or MIP-1β levels. To establish the MMR, TARC levels and/or MIP-1β levels of a normal individual, an individual or group of individuals may be first assessed for PTSD to establish that the individual or group of individuals is not suffering from PTSD. Once established, the MMR of the individual or group of individuals can then be determined to establish a "normal" MMR, TARC levels and/or MIP-1β levels. In one embodiment, normal MMR, TARC levels and/or MIP-1β levels can be ascertained from the same subject when the subject is deemed to not be suffering from or exhibiting sign (clinical or otherwise) of PTSD. In one embodiment, a "normal" MMR, TARC levels and/or MIP-1β levels is(are) assessed in the same subject from whom the sample is taken prior to the onset of measureable, perceivable or diagnosed PTSD. That is, the term "normal" with respect to MMR, TARC levels and/or MIP-1β levels can be used to mean the subject's baseline MMR, TARC levels and/or MIP-1β levels prior to the onset of PTSD. The MMR, TARC levels and/or MIP-1β levels can then be reassessed periodically and compared to the subject's baseline MMR, TARC levels and/or MIP-1β levels. Thus, the present invention also include methods of monitoring the progression of PTSD in a subject (including monitoring the effectiveness of a treatment of PTSD), with the methods comprising determining the subject's MMR, TARC levels and/or MIP-1β levels more than once over a period of at least more than one day. As used herein, a "day" is a 24-hour time period, not necessarily a different calendar day. For example, some embodiments of the methods of the present invention will comprise determining the subject's MMR, TARC levels and/or MIP-1β levels two, three, four, five, six, seven, eight, nine, 10 or even more times over a period of time, such as a year, two years, three, years, four years, five years, six years, seven years, eight years, nine years or even 10 years or longer. The methods of monitoring a subject's risk of suffering from PTSD would also include embodiments in which the subject's MMR, TARC levels and/or MIP-1β levels is(are) assessed during and after treatment of PTSD. In other words, the present invention also includes methods of monitoring the efficacy of treatment of PTSD by assessing the subject's MMR, TARC levels and/or MIP-1β levels over the course of the treatment and after the treatment. The treatment may be any treatment designed to treat the symptoms or root cause of MMR.

In another embodiment, a normal MMR, TARC levels and/or MIP-1β levels is (are) assessed in a sample from a different subject or patient (from the subject being analyzed) and this different subject does not have or is not suspected of having PTSD. In still another embodiment, the normal MMR, TARC levels and/or MIP-1β levels is(are) assessed in a population of healthy individuals, the constituents of which display no signs of PTSD. Thus, the subject's MMR, TARC levels and/or MIP-1β levels can be compared to normal MMR, TARC levels and/or MIP-1β levels generated from a single normal sample or MMR, TARC levels and/or MIP-1β levels generated from more than one normal sample.

The invention also relates to methods of monitoring the progression of post-traumatic stress disorder (PTSD) in a subject, with the methods comprising determining the MMR, TARC levels and/or MIP-1β levels in the subject on at least two different days and comparing the MMRs, TARC levels and/or MIP-1β levels over time to determine if the subject's MMR, TARC levels and/or MIP-1β levels is(are) changing over time. An increase in the subject's MMR and/or MIP-1β levels over time is indicative that the PTSD is progressing in the subject. A decrease in the subject's TARC levels over time is indicative that the PTSD is progressing in the subject.

The invention also relates to methods of diagnosing post-traumatic stress disorder (PTSD) in a subject, with the methods comprising determining the MMR, TARC levels and/or MIP-1β levels in the subject and comparing the MMR, TARC levels and/or MIP-1β levels to normal MMR, TARC levels and/or MIP-1β levels. An elevation in the MMR and/or MIP-1β levels over a normal MMR and/or MIP-1β levels is indicative that the subject has or is suffering from PTSD. A decrease in TARC levels over normal TARC levels is indicative that the subject has or is suffering from PTSD.

The invention also relates to methods of treating a subject with post-traumatic stress disorder (PTSD), with the methods comprising determining that the subject has PTSD by using the methods of the invention described herein and administering to the subject with PTSD a therapeutic regimen to treat the PTSD. A therapeutic regimen used to treat PTSD includes but is not limited to, cognitive behavioral therapy (CBT), administration of one more selective serotonin reuptake inhibitors (SSRIs), administration of one or more anti-anxiety medications and administration of one or more anti-insomnia medications. Specifically, the methods of treatment comprise determining the MMR, TARC levels and/or MIP-1β levels in a sample obtained from the subject, and comparing the MMR, TARC levels and/or MIP-1β levels in the sample to a normal MMR, TARC levels and/or MIP-1β levels to determine if the subject's MMR, TARC levels and/or MIP-1β levels is altered compared to the normal MMR, TARC levels and/or MIP-1β levels, where a change in the subject's MMR compared to those defined as having a normal MMR is indicative that the subject is suffering from PTSD. An elevation in the MMR and/or MIP-1β levels over a normal MMR and/or MIP-1β levels is indicative that the subject has or is suffering from PTSD. A decrease in TARC levels over normal TARC levels is indicative that the subject has or is suffering from PTSD. Subsequent to this determination, the subject is administered a therapeutic regimen for treating PTSD.

In select embodiments, the SSRIs that are administered to the subject suffering from PTSD are selected from the group consisting of citalopram, dapoxetine, escitalopram, fluoxetine, fluvoxamine, indalpine, paroxetine, sertraline and zimelidine.

The invention also relates to kits that can be used in the methods of the present invention. Specifically, the present invention provides kits for the diagnosis, monitoring and/or treatment of PTSD, with the kits comprising one or more sets of antibodies that are immobilized onto a solid substrate and specifically bind to at least one of MCP-1, MCP-4, TARC and MIP-1β. In specific embodiments, the kits comprise at least two sets of antibodies immobilized onto a solid substrate, with one set of antibodies directed towards MCP-1 and the second set of antibodies being directed towards MCP-4. In specific embodiments, the kits comprise at least four sets of antibodies immobilized onto a solid substrate, with one set of antibodies directed towards MCP-1, the second set of antibodies being directed towards MCP-4, the third set of antibodies directed towards TARC and the fourth set of antibodies being directed towards MIP-1β.

The antibodies that are immobilized onto the substrate may or may not be labeled. For example, the antibodies may be labeled, e.g., bound to a labeled protein, in such a manner that binding of the specific protein may displace the label and the presence of the marker in the sample is marked by the absence of a signal. In addition, the antibodies that are immobilized onto the substrate may be directly or indirectly immobilized onto the surface. Methods for immobilizing proteins, including antibodies, are well-known in the art, and such methods may be used to immobilize a target protein, e.g., TARC, or another antibody onto the surface of the substrate to which the antibody directed to the specific biomarker can then be specifically bound. In this manner, the antibody directed to the specific biomarker is immobilized onto the surface of the substrate for the purposes of the present invention.

The kits of the present invention may or may not include containers for collecting samples from the subject and one or more reagents, e.g., purified target biomarker such as MCP-1, MCP-4, TARC or MIP-1β, for preparing a calibration curve. The kits may or may not include additional reagents such as wash buffers, labeling reagents and reagents that are used to detect the presence (or absence) of the label.

EXAMPLES

Example 1—Methods and Materials

Twelve medication-free outpatients with chronic civilian PTSD (median age years old, 8 women/4 men) and eleven non-traumatized, healthy subjects (median age 29.5 years old, 5 women, 5 men) were selected from the original cohort study.

The healthy control subjects were chosen to match PTSD patients as closely as possible with respect to age, sex and BMI. In the subset of PTSD patients studied here, prodromal PTSD traumas were prepubertal in 5 subjects and as adults for 7 subjects. Time elapsed from trauma exposure was 26±4 years in pre-pubertal trauma, and 10.1±8.8 years in adult exposure. Patients were otherwise physically healthy, did not meet criteria for alcohol or substance abuse, or dependence, for at least six months prior to the study and were not receiving psychotropic medication for at least three weeks prior to lumbar puncture and concomitant venipuncture. The required medication-free period for PTSD patients, however, was extended to six weeks for patients previously taking fluoxetine or other SSRI. In addition, four patients (three female and one male) were included who had a history of trauma but without a follow-on history of PTSD. Although these latter patients were not included in the study, the data for these "trauma controls" were not statistically different from the healthy controls.

Psychiatric diagnoses were established using the Structured Clinical Interview for DSM-IV (SCID). The severity of PTSD was determined using the Clinician-Administered PTSD Scale (CAPS). Severity of depressive, anxiety and overall symptoms was assessed using the Inventory of Depressive Symptomatology (IDS), Hamilton Anxiety Rating Scale (HAMA) and Clinical Global Impression-Severity scale (CGI-S), respectively. Individuals with PTSD and controls did not differ with regard to age, gender distribution, race, or body mass index (BMI). The severity of PTSD was moderate, with a CAPS score of 73.1±10.3. The severity of depression (IDS 16.4±8.2), anxiety (HAMA 13.1±6.8) and overall symptoms (CGI-S 4±1.2) were moderate as well.

Blood samples were collected from PTSD and healthy control patients. For this study, patients were implanted with indwelling intravenous catheters, and blood was collected each hour over a 27-hour period. There were at least two 9 AM time points in the entire plasma collection process, and samples from the second 9 AM time point were chosen for analysis. Care was taken to ensure that blood samples, drawn by hand from the indwelling catheter, were immediately anti-coagulated with sodium citrate, and plasma collected by centrifugation. Care was also taken to ensure that nighttime sampling was done without disturbing the patient. Following immediate centrifugation, supernatant solutions were split and stored at −80° C.

Lumbar puncture (LP) was performed between 8:00 and 9:00 AM by an experienced physician. A 20-gauge introducer needle was inserted and approximately 15 cc of CSF was withdrawn, centrifuged at 4,000 RPM and frozen in aliquots at −80° C. The LPs were drawn on different days than the plasma collection.

Two multiplexed assays for cytokines and chemokines were used for analysis of patient and control plasma samples on the SECTOR® Imager 6000 instrument (Meso Scale Discovery, Gaithersburg, Md.) The first of these assays was the Human ProInflammatory 9 Plex Assay for the measurement of IL-2, IL-8, IL-12p70, IL-1β, GM-CSF, IFN-γ, IL-6, IL-10 and TNF-α (MesoScale catalog #K15007C-4). The second of these assays was the Human Chemokine 9 Plex Assay for the measurement of Eotaxin 1, MIP-1β, Eotaxin-3, TARC, IP-10, IL-8, MCP-1 (CCL2), MDC, and MCP-4 (CCL13) (catalog #K15001C-1). The samples were added to plates that were pre-coated with capture antibodies for the specific cytokines. The plates was sealed and shaken at room temperature for two hours. The plates were the washed in PBS+0.05% Tween-20 and detection antibody solution (1× or 1 µg/mL) was then added. The plates were sealed and shaken at room temperature for two hours. The plate was then washed in PBS+0.05% Tween-20. Read buffer was added at a 2× concentration, and the plate was read on the SECTOR® 6000 Imager.

Data points were characterized on the basis of reproducible technical replicates, low % coefficient of variation (CV<5%) present within the linear portion of the standard curve and a value above the lower limit of detection (LLOD). The differences between PTSD samples and normal controls were calculated using a 2-tailed t-test and were taken as significant at the p≤0.05 level or more than 2 standard deviations from the mean (SD≥2.0), as appropriate. Values for all analytes from CSF for healthy controls were statistically indistinguishable from data published by others who had also used the industry-standard MesoScale electrochemiluminescence Sector 6000 platform for analysis [23-26]. For analysis of the relative circadian variation, values for individual patients were normalized to their individual 24 hour means, and changes for each patient were calculated as a percentage. The percentages were added for each hour to create composite profiles for PTSD and healthy control patients. Times were standardized to the sunrise time on the day blood sampling began (Z=0, the Zeitgeber). Circadian rhythms were modeled by fitting data to a cosine function.

Example 2—Results

Table 2 below shows measurements of cytokines and chemokines in plasma collected from both PTSD and healthy control patients at the 9 AM time point. MCP-4 was significantly elevated by about 43%. The p value is 0.01 and the area under the curve ("AUC") is 0.82. In contrast, MCP-1 was reduced by about 20%. The AUC value is also 0.82. The MCP-1 and MCP-4 data thus stratify in opposite directions.

As shown in the last row in Table 2, by dividing these two inversely directional classifiers, the MCP-4/MCP-1 ratio was elevated 84% in PTSD plasma, and provides a highly significant candidate metric for PTSD plasma collected at 9 AM. The difference is significant, based on both a low p value of 0.004 and a high AUC value of 0.84. This PTSD-specific metric has a higher value at 9 AM than 2 AM (see below), indicating that the signal may be diurnal.

TABLE 2

| Analyte | PTSD[1] | HC[1] | p-value[2] | Ratio[3] | AUC[4] |
| --- | --- | --- | --- | --- | --- |
| GM-CSF | ~LLOD | ~LLOD | n.a. | n.a. | n.a. |
| IFN-γ | ~LLOD | ~LLOD | n.a. | n.a. | n.a. |
| IL-10 | 0.79 ± 0.24 | 0.69 ± 0.32 | 0.21 | ≈1.15 ± 0.60 | 0.69 |
| IL-12 p70 | ~LLOD | ~LLOD | n.a. | n.a | n.a. |
| IL-1β | 0.08 ± 0.02 | 0.18 ± 0.04 | 0.04 | ↓ 2.12 ± 0.63 | 0.71 |
| IL-2 | 0.15 ± 0.04 | 0.17 ± 0.05 | 0.72 | ≈0.93 ± 0.38 | 0.55 |
| IL-6 | 0.47 ± 0.04 | 0.77 ± 0.16 | 0.15 | ↓ 1.62 ± 0.33 | 0.74 |
| IL-8 | 1.67 ± 0.56 | 1.98 ± 0.59 | 0.67 | ≈0.84 ± 0.37 | 0.52 |
| TNF-α | 2.57 ± 0.41 | 1.57 ± 0.22 | 0.03 | ↑ 1.64 ± 0.34 | 0.76 |
| Eotaxin | 503.45 ± 37.95 | 496.61 ± 37.29 | 0.91 | ≈1.01 ± 0.11 | 0.52 |
| Eotaxin-3 | 6.90 ± 0.55 | 6.42 ± 0.38 | 0.58 | ≈1.07 ± 0.10 | 0.63 |
| IP-10 | 226.06 ± 30.53 | 149.66 ± 13.37 | 0.04 | ↑ 1.51 ± 0.24 | 0.73 |
| MCP-1 | 171.11 ± 17.01 | 207.10 ± 17.49 | 0.14 | ≈0.83 ± 0.11 | 0.82 |
| MCP-4 | 298.35 ± 27.00 | 208.62 ± 23.94 | 0.01 | ↑ 1.43 ± 0.20 | 0.77 |
| MDC | 1850.02 ± 155.12 | 1680.60 ± 167.21 | 0.40 | ≈1.10 ± 0.14 | 0.61 |
| MIP-1β | 65.85 ± 8.12 | 55.58 ± 4.77 | 0.36 | ≈1.18 ± 0.17 | 0.66 |
| TARC | 85.52 ± 13.86 | 67.32 ± 10.24 | 0.30 | ↑ 1.27 ± 0.28 | 0.70 |
| MCP1/MCP4 | 0.61 ± 0.06 | 1.12 ± 0.18 | 4E−03 | ↓ 1.84 ± 0.33 | 0.84 |
| MCP4/MCP1 | 1.82 ± 0.19 | 1.10 ± 0.16 | 4E−03 | ↑ 1.66 ± 0.28 | 0.84 |

Several other individual cytokines and chemokines were also significantly different in the PTSD 9 AM plasmas compared to healthy control plasmas. Significantly different cytokines and chemokines included IL-1β (reduced more than 2-fold; p=0.04; AUC=0.71); TNF-α (elevated about 64%; p=0.03; AUC=0.76); and IP-10 (elevated about 50%; p=0.04; AUC=0.73). Nonetheless, while these differences were significant, they were relatively modest, and the AUC values calculated from the receiver operation condition (ROC) were also modest.

Measurement of Cytokines and Chemokines in PTSD Plasma at 2 AM

Table 3 below shows measurements of cytokines and chemokines in plasma collected from both PTSD and healthy control patients at 2 AM. The table indicates that the two analytes, MCP-1 and MCP-4, still varied in opposite directions, and each was among the highest AUC values on the list. For the case of PTSD, the last row in Table 3 shows that the MCP-4/MCP-1 ratio was elevated 34% in plasma from PTSD patients compared to healthy controls. The P value, based on a two-tailed t-test, was 0.02, and the ROC curve has an AUC of 0.75. The multiparameter analysis thus also identified the MCP-4/MCP-1 ratio as a candidate binary classifier for PTSD and healthy controls in both 9 AM and 2 AM plasma samples.

TABLE 3

| Analyte | PTSD[1] | HC[1] | p-value[2] | Ratio[3] | AUC[4] |
| --- | --- | --- | --- | --- | --- |
| GM-CSF | 0.39 ± 0.06 | 0.49 ± 0.09 | 0.50 | ≈0.81 ± 0.18 | 0.63 |
| IFN-γ | 1.01 ± 0.15 | 1.01 ± 0.15 | 0.96 | ≈1.00 ± 0.20 | 0.56 |
| IL-10 | 2.45 ± 0.64 | 1.76 ± 0.56 | 0.22 | ↑ 1.40 ± 0.55 | 0.65 |
| IL-12 p70 | 1.21 ± 0.37 | 0.67 ± 0.15 | 0.46 | ↑ 1.82 ± 0.66 | 0.53 |
| IL-1β | 0.16 ± 0.03 | 0.22 ± 0.04 | 0.14 | ↓ 1.35 ± 0.36 | 0.68 |
| IL-2 | 0.31 ± 0.07 | 0.40 ± 0.06 | 0.11 | ↓ 1.29 ± 0.34 | 0.78 |
| IL-6 | 1.58 ± 0.31 | 2.09 ± 0.43 | 0.17 | ↓ 1.32 ± 0.36 | 0.68 |
| IL-8 | 2.63 ± 0.65 | 2.52 ± 0.41 | 0.84 | ≈1.05 ± 0.30 | 0.57 |
| TNF-α | 4.28 ± 0.52 | 3.91 ± 0.61 | 0.41 | ≈1.10 ± 0.21 | 0.55 |
| Eotaxin | 529.42 ± 68.32 | 520.09 ± 90.82 | 0.71 | ≈1.02 ± 0.21 | 0.52 |
| Eotaxin-3 | 5.54 ± 0.75 | 6.61 ± 1.01 | 0.25 | ≈0.84 ± 0.17 | 0.61 |
| IP-10 | 287.02 ± 49.92 | 197.54 ± 37.57 | 0.07 | ↑ 1.45 ± 0.36 | 0.70 |
| MCP-1 | 292.69 ± 35.35 | 333.08 ± 49.15 | 0.47 | ≈0.88 ± 0.16 | 0.67 |
| MCP-4 | 375.52 ± 48.01 | 320.24 ± 59.16 | 0.22 | ≈1.17 ± 0.25 | 0.65 |
| MDC | 3807.36 ± 656.11 | 2962.75 ± 470.42 | 0.24 | ↑ 1.29 ± 0.29 | 0.61 |
| MIP-1β | 78.53 ± 10.84 | 93.43 ± 15.21 | 0.34 | ≈0.84 ± 0.17 | 0.61 |
| TARC | 87.96 ± 14.02 | 108.58 ± 19.72 | 0.38 | ≈0.81 ± 0.19 | 0.59 |
| MCP1/MCP4 | 0.74 ± 0.09 | 1.02 ± 0.15 | 0.02 | ↓ 1.38 ± 0.25 | 0.74 |
| MCP4/MCP1 | 1.20 ± 0.15 | 0.90 ± 0.14 | 0.02 | ↑ 1.34 ± 0.26 | 0.75 |

[1]average ± sem, pg/ml
[2]two-tailed t-test
[3]↑ PTSD > HC; ↓ PTSD < HC
[4]Area Under the Curve of the ROC Curve
~LLOD: (viz, the analyte was too low in either the plasma or the CSF to calculate accurately
n.a.: not available.

Table 4 shows measurements of cytokines and chemokines in CSF, which were collected from both PTSD and healthy control patients at the 9 AM time point. Of the complete set of analytes, only reduction of IL-8 was able to approach significance in PTSD CSF. While IL-8 in PTSD CSF was reduced by about 25%, the p value (two tailed) was 0.06. Surprisingly, the MCP-4 and MCP-1 levels in the 9 AM CSF samples were the reverse of those found in plasma, and independent of PTSD. Specifically, in healthy control CSF, the MCP-1 levels were about 7-fold higher than in plasma, while the MCP-4 levels were about 100-fold lower. Furthermore, the MCP-4/MCP-1 ratio in CSF did not significantly discriminate between PTSD and healthy control patients, as it does in the 2 AM or 9 AM plasma samples.

TABLE 4

| Analyte | PTSD[1] | HC[1] | p-value[2] | Ratio[3] | AUC[4] |
| --- | --- | --- | --- | --- | --- |
| GM-CSF | ~LLOD | ~LLOD | n.a. | n.a. | n.a. |
| IFN-γ | ~LLOD | ~LLOD | n.a. | n.a. | n.a. |
| IL-10 | 0.79 ± 0.24 | 0.69 ± 0.32 | 0.21 | ≈1.15 ± 0.60 | 0.69 |
| IL-12 p70 | ~LLOD | ~LLOD | n.a. | n.a | n.a. |
| IL-1β | 0.08 ± 0.02 | 0.18 ± 0.04 | 0.04 | ↓ 2.12 ± 0.63 | 0.71 |
| IL-2 | 0.15 ± 0.04 | 0.17 ± 0.05 | 0.72 | ≈0.93 ± 0.38 | 0.55 |
| IL-6 | 0.47 ± 0.04 | 0.77 ± 0.16 | 0.15 | ↓ 1.62 ± 0.33 | 0.74 |
| IL-8 | 1.67 ± 0.56 | 1.98 ± 0.59 | 0.67 | ≈0.84 ± 0.37 | 0.52 |
| TNF-α | 2.57 ± 0.41 | 1.57 ± 0.22 | 0.03 | ↑ 1.64 ± 0.34 | 0.76 |
| Eotaxin | 503.45 ± 37.95 | 496.61 ± 37.29 | 0.91 | ≈1.01 ± 0.11 | 0.52 |

TABLE 4-continued

| Analyte | PTSD[1] | HC[1] | p-value[2] | Ratio[3] | AUC[4] |
|---|---|---|---|---|---|
| Eotaxin-3 | 6.90 ± 0.55 | 6.42 ± 0.38 | 0.58 | ≈1.07 ± 0.10 | 0.63 |
| IP-10 | 226.06 ± 30.53 | 149.66 ± 13.37 | 0.04 | ↑ 1.51 ± 0.24 | 0.73 |
| MCP-1 | 171.11 ± 17.01 | 207.10 ± 17.49 | 0.14 | ≈0.83 ± 0.11 | 0.82 |
| MCP-4 | 298.35 ± 27.00 | 208.62 ± 23.94 | 0.01 | ↑ 1.43 ± 0.20 | 0.77 |
| MDC | 1850.02 ± 155.12 | 1680.60 ± 167.21 | 0.40 | ≈1.10 ± 0.14 | 0.61 |
| MIP-1β | 65.85 ± 8.12 | 55.58 ± 4.77 | 0.36 | ≈1.18 ± 0.17 | 0.66 |
| TARC | 85.52 ± 13.86 | 67.32 ± 10.24 | 0.30 | ↑ 1.27 ± 0.28 | 0.70 |
| MCP1/MCP4 | 0.61 ± 0.06 | 1.12 ± 0.18 | 4E−03 | ↓ 1.84 ± 0.33 | 0.84 |
| MCP4/MCP1 | 1.82 ± 0.19 | 1.10 ± 0.16 | 4E−03 | ↑ 1.66 ± 0.28 | 0.84 |

[1]average ± sem, pg/ml
[2]two-tailed t-test
[3]↑ PTSD > HC; ↓ PTSD < HC
[4]Area Under the Curve of the ROC Curve
~LLOD: (viz, the analyte was too low in either the plasma or the CSF to calculate accurately
n.a.: not available FIG. 1 shows the dot-plot distributions of MCP-1 (FIG. 1: a, b and c), MCP-4 (FIG. 1: c, d and e) and the MCP-4/MCP-1 ratio (FIG. 1: f, g and h) in PTSD and healthy control plasma at 2 AM and 9 AM, and in CSF at 9 AM, respectively. The MCP-1 levels in the 2 AM (FIG. 1a) and the 9 AM (FIG. 1b) plasma samples trend lower than levels for the healthy controls.

In contrast, in the 9 AM CSF (FIG. 1c), the MCP-1 levels were similar for both PTSD and healthy controls, and were about 7 fold greater than MCP-1 levels in the parallel 9 AM plasma samples. On the other hand, FIG. 1d (plasma 2 AM) and FIG. 1e (plasma 9 AM) show that MCP-4 was elevated in PTSD plasma. However, levels of MCP-4 were similar in both PTSD and healthy controls in 9 AM CSF (FIG. 1f), and contained about 100-fold less MCP-4 than in parallel 9 AM plasma from either cohort. The MCP-4/MCP-1 ratio at 2 AM (FIG. 1g) and 9 AM (FIG. 1h) were elevated in PTSD plasma, but was low in the 9 AM CSF (FIG. 1i).

Figure 4A:
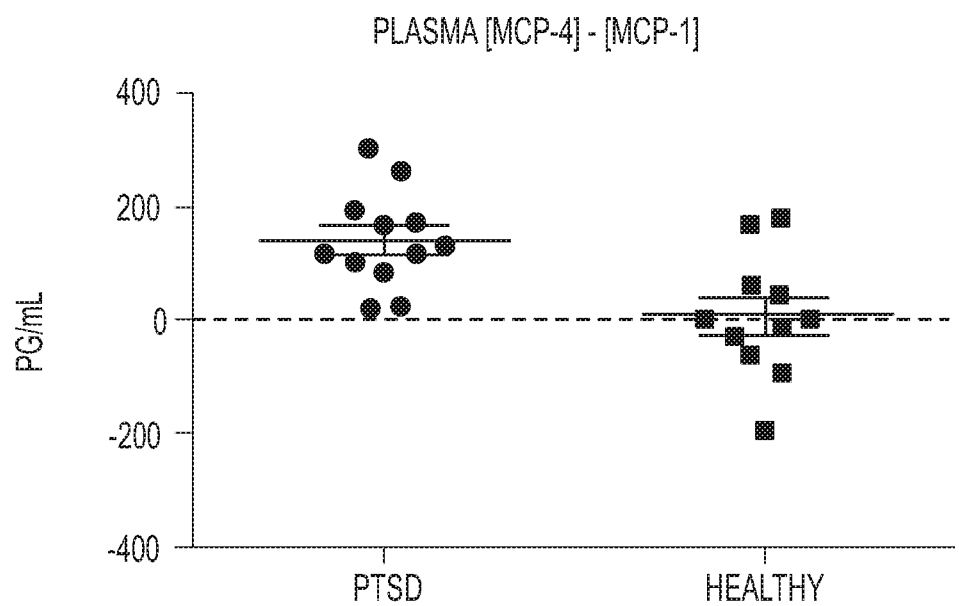
FIG. 4 (A-B) depicts the plasma concentrations of MCP-4 and MCP-1 in PTSD patients and healthy controls. (a) absolute concentrations; (b) average concentrations FIG. 5 (A-D) depicts area under the curve (AUC) for receiver operator curves (ROCs) for embodiments of the present invention.
Figure 4B:
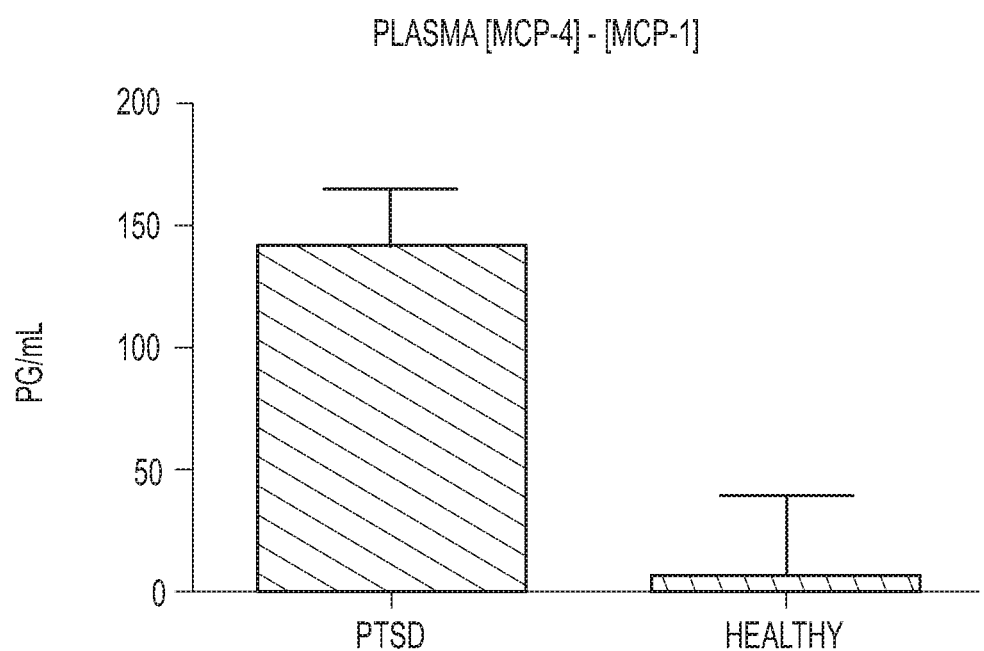
Figure 5B:
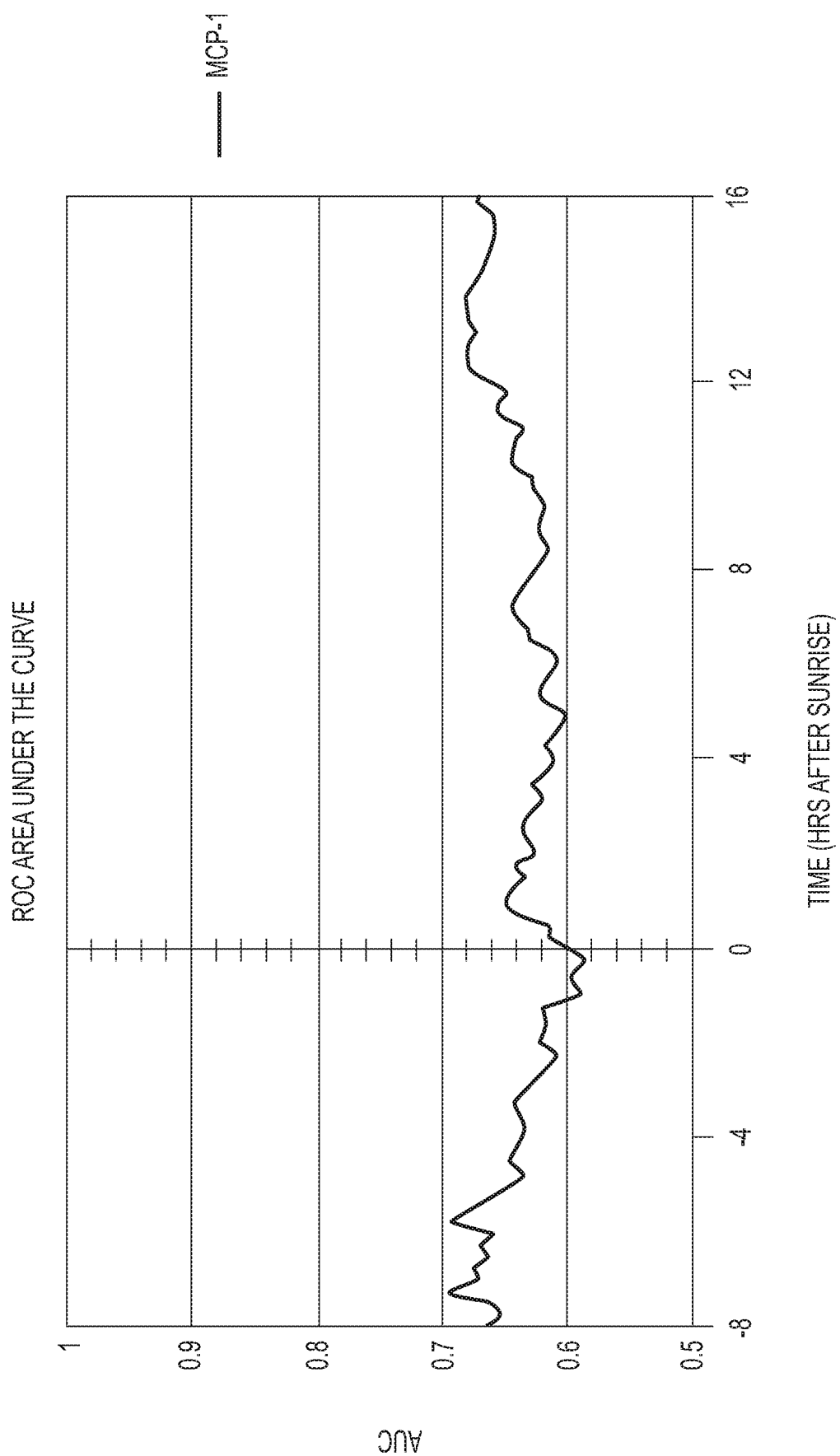
Figure 5C:
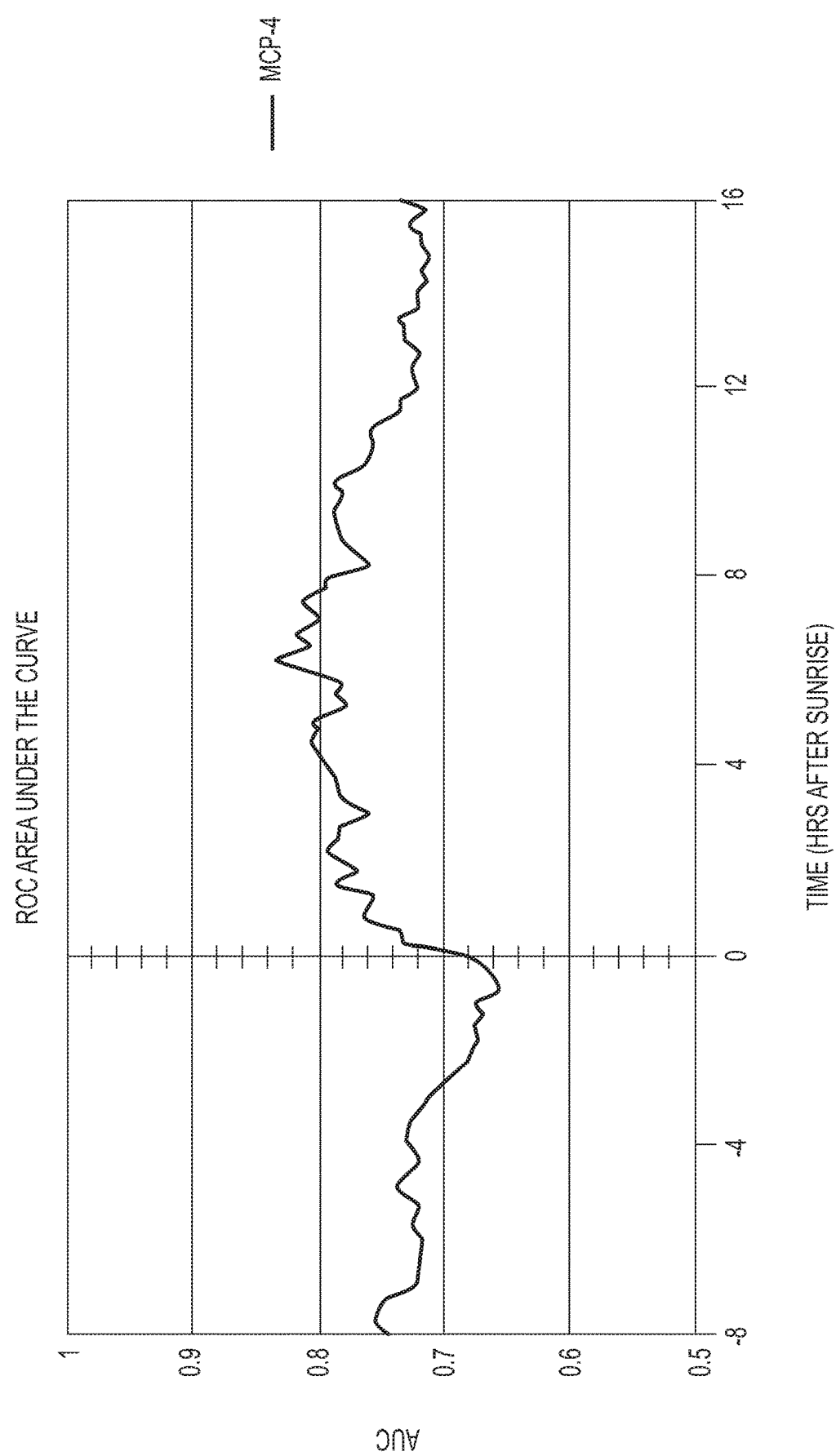
Figure 5D:
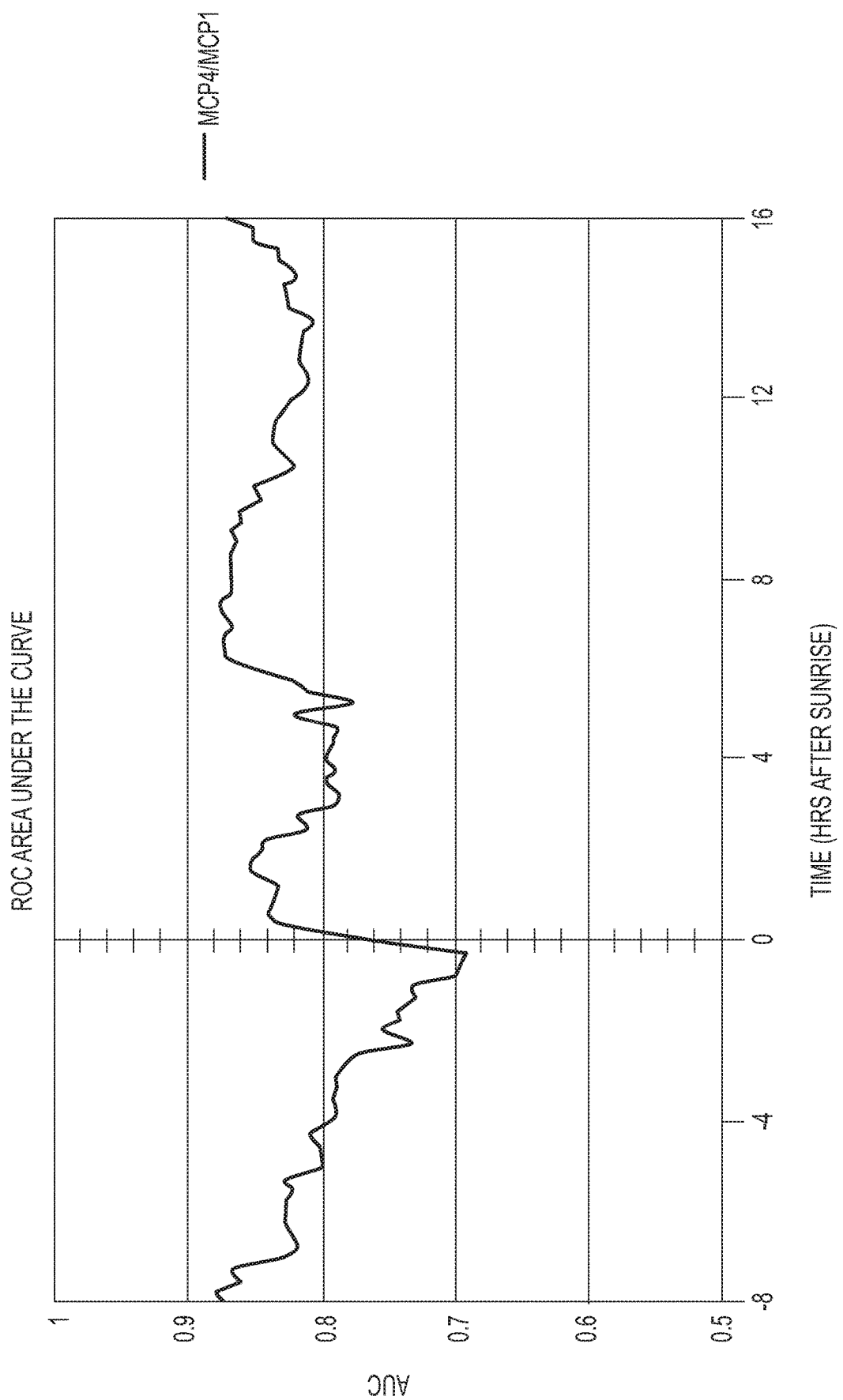
Figure 6:
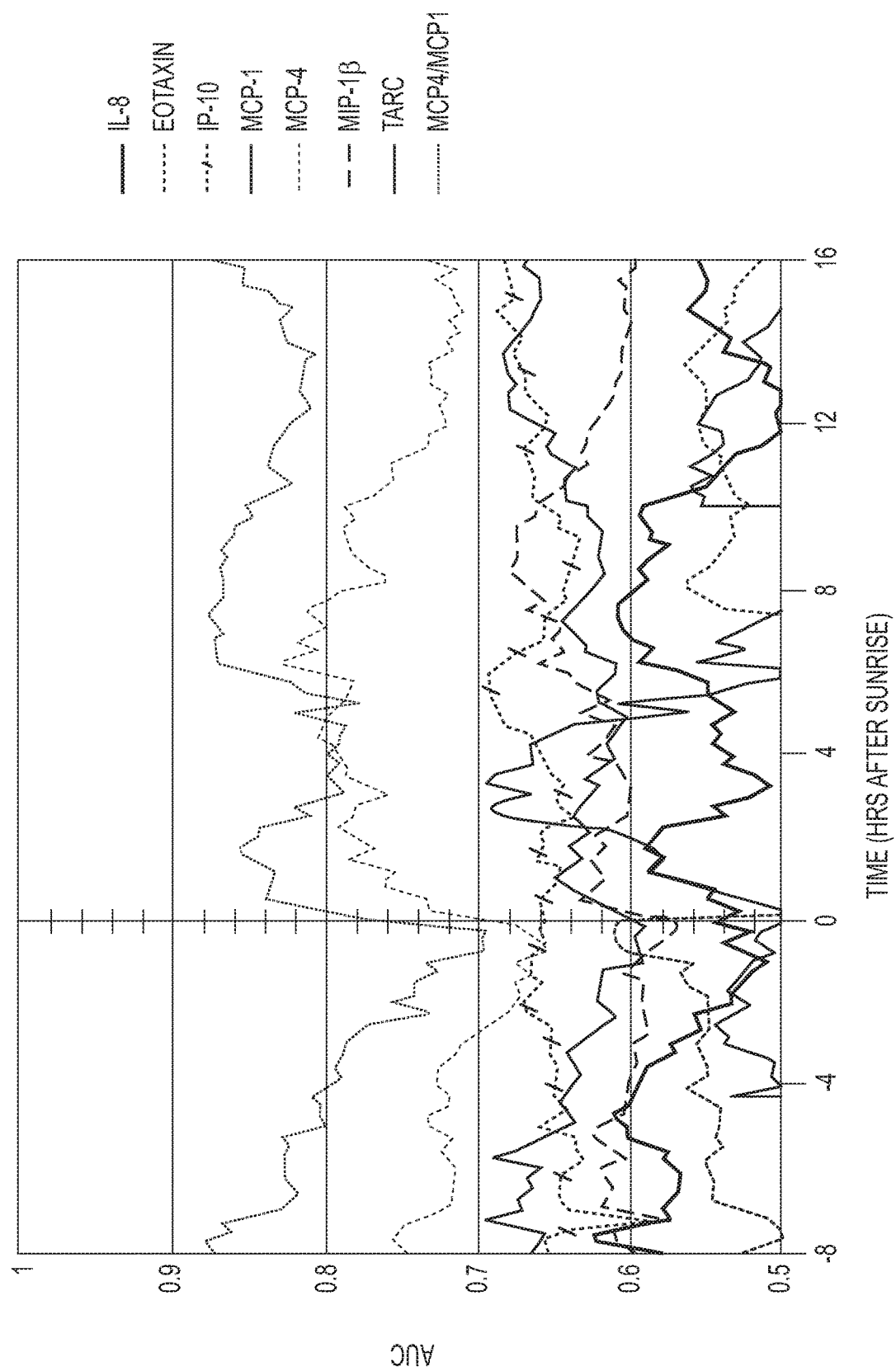
FIG. 6 depicts the AUC for ROCs for various chemokines.
Figure 7A:
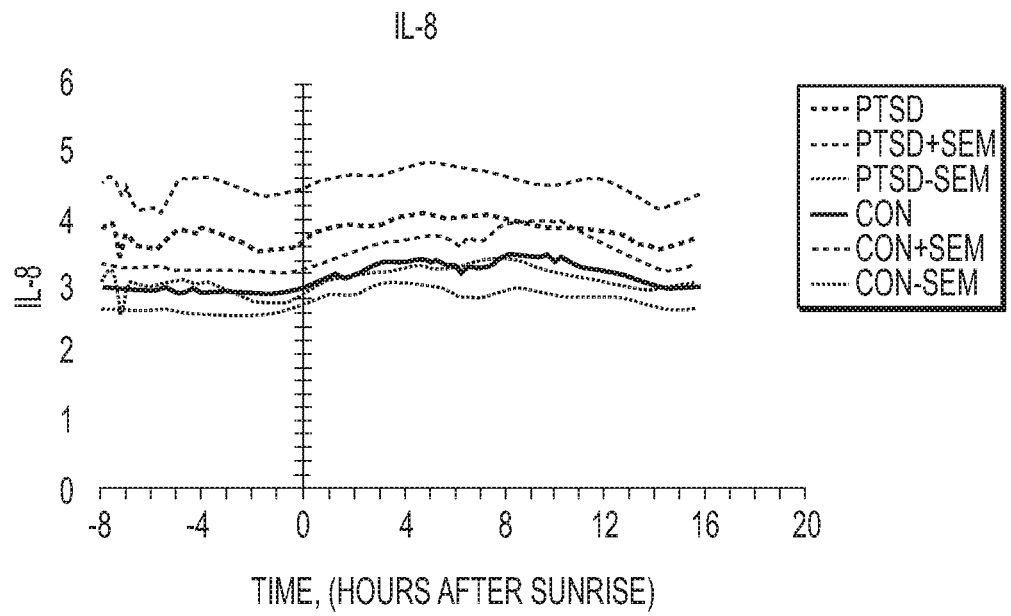
FIG. 7 (A-H) depicts circadian dependence of plasma chemokines in PTSD and controls.
Figure 7A:
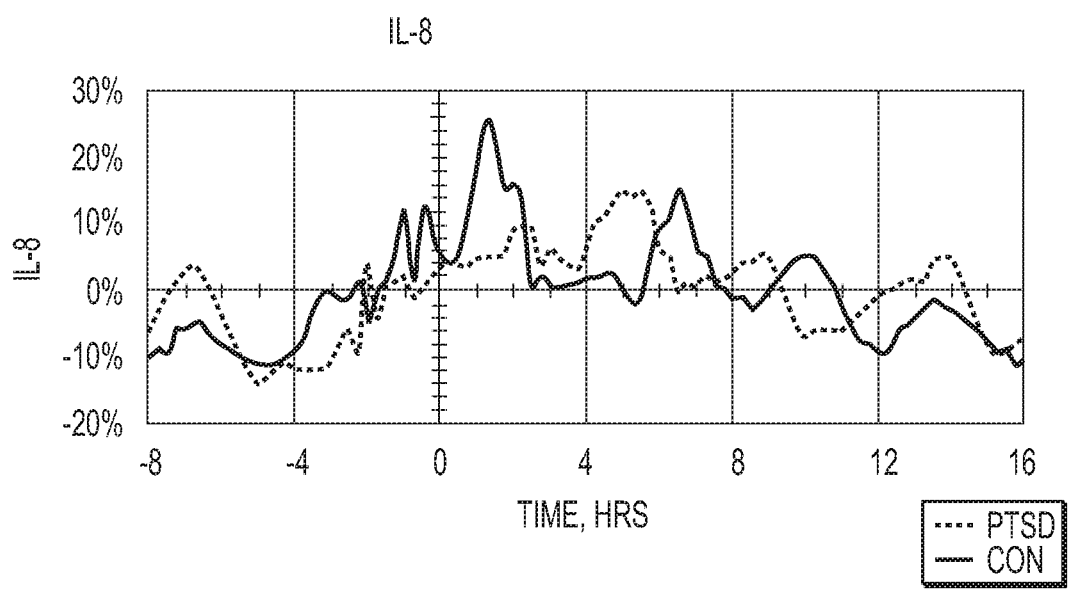
Figure 7B:
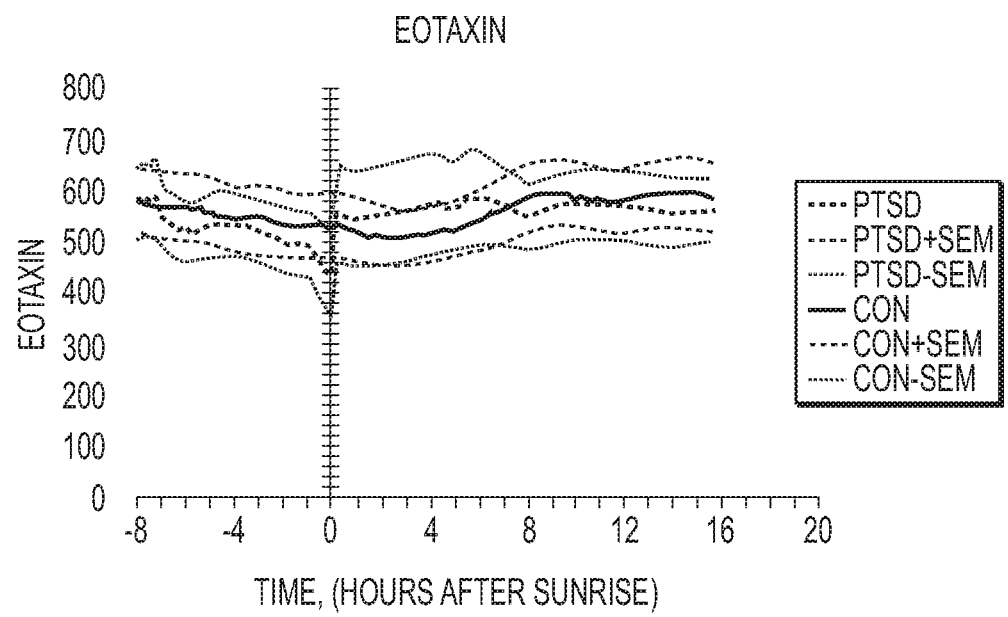
Figure 7B:
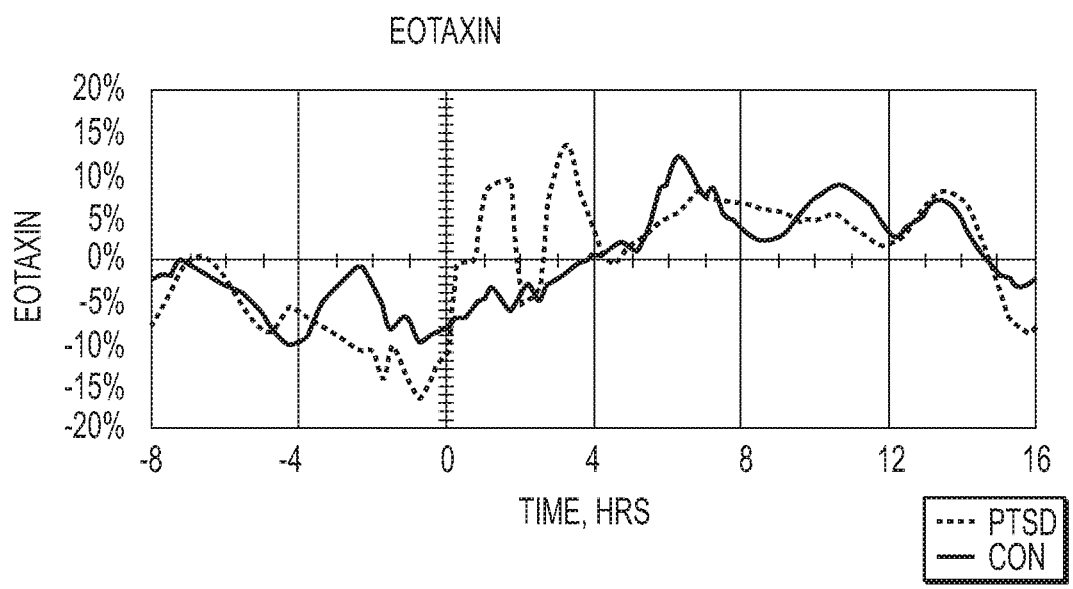
Figure 7C:
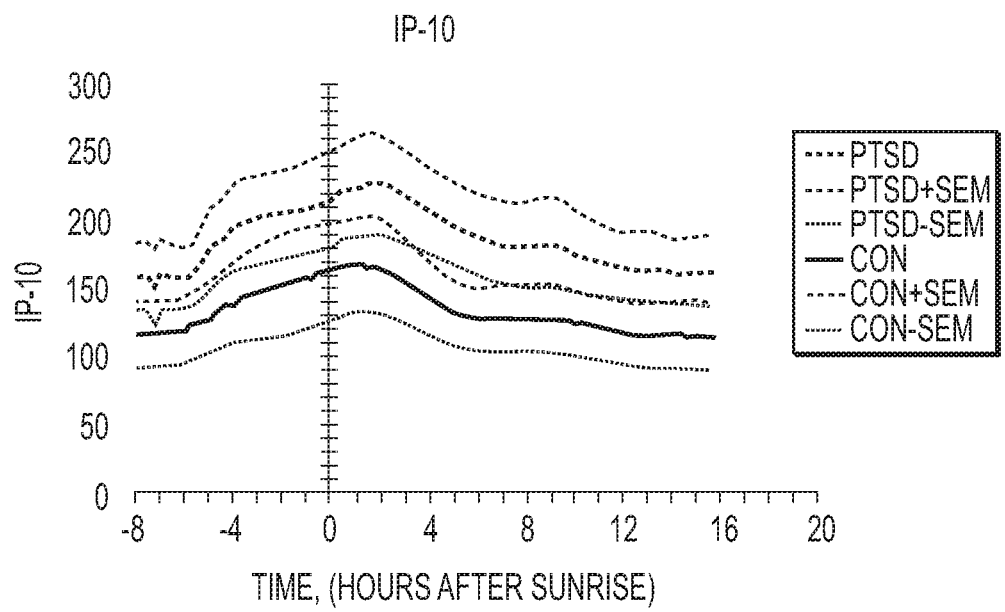
Figure 7C:
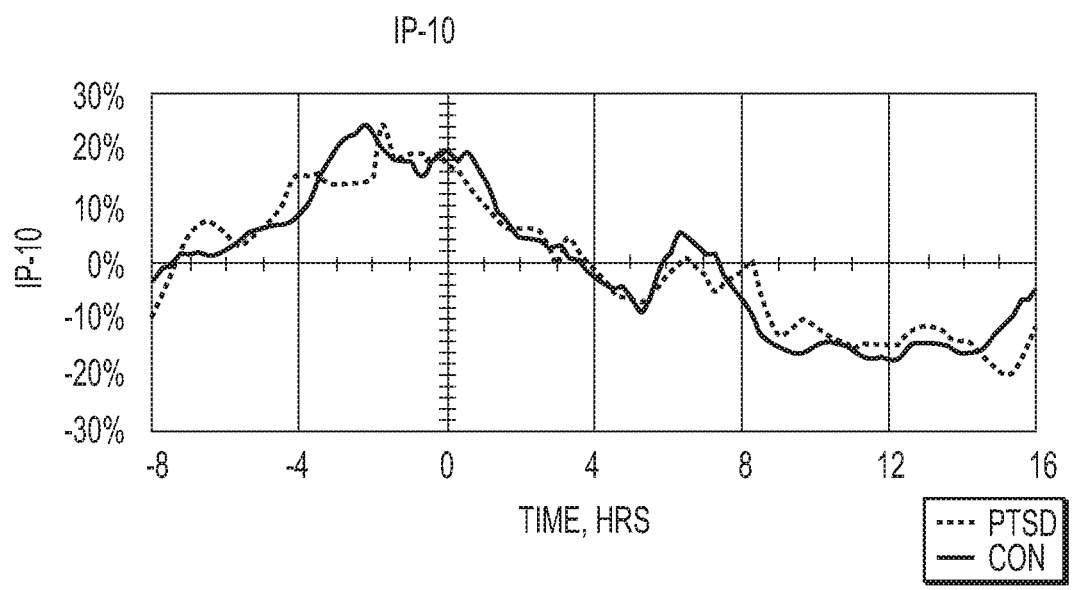
Figure 7D:
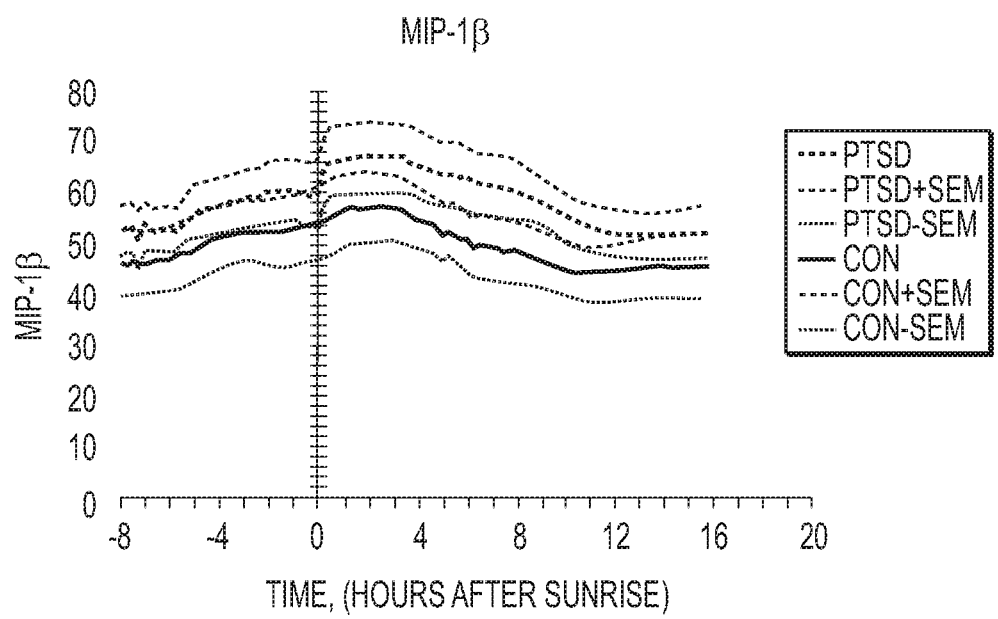
Figure 7D:
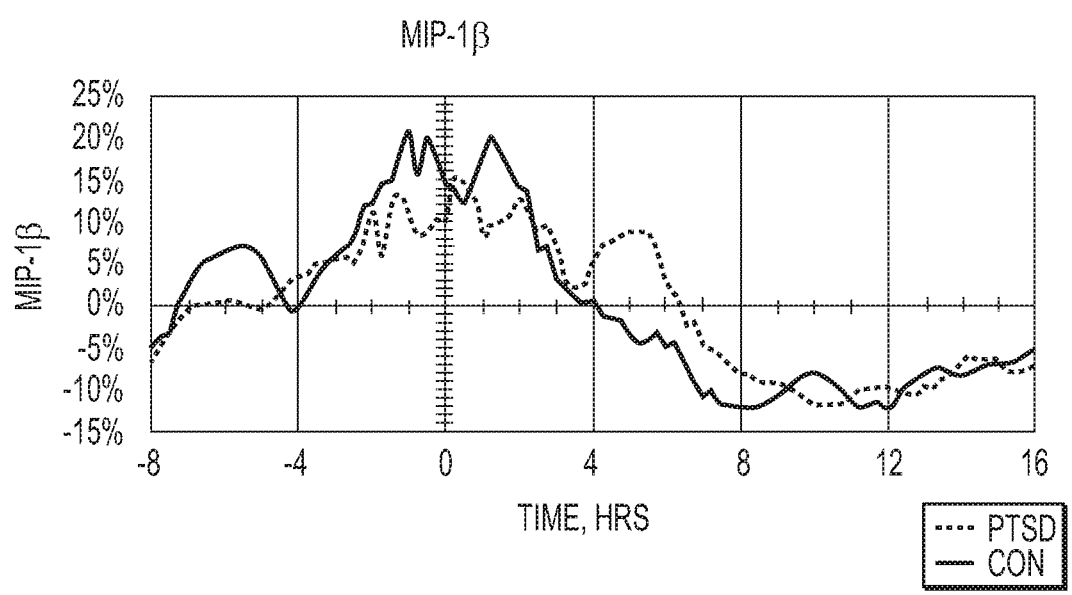
Figure 7E:
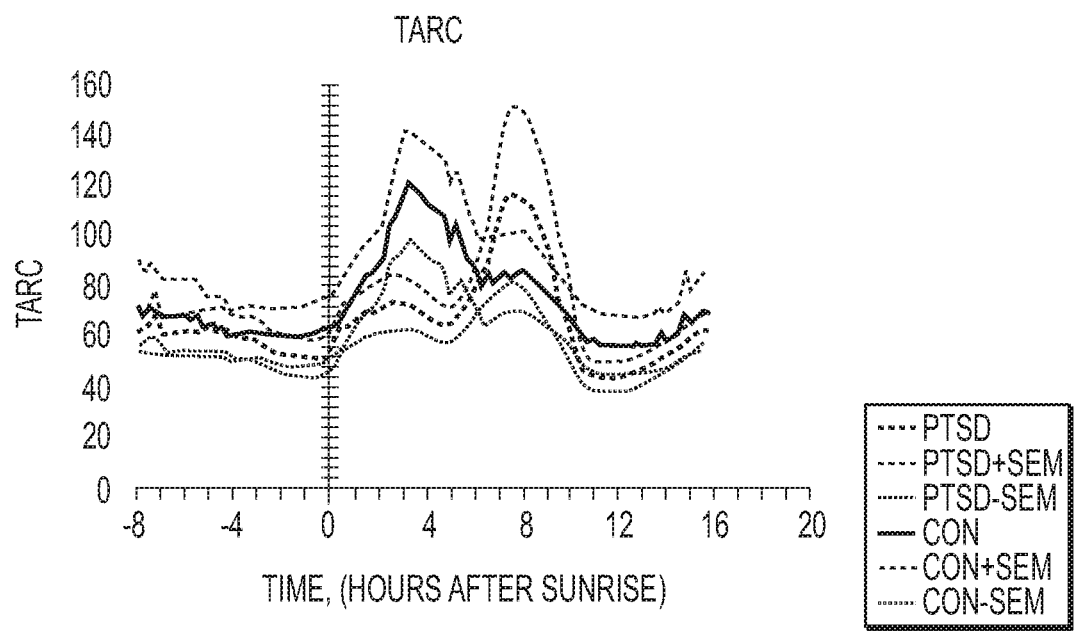
Figure 7E:
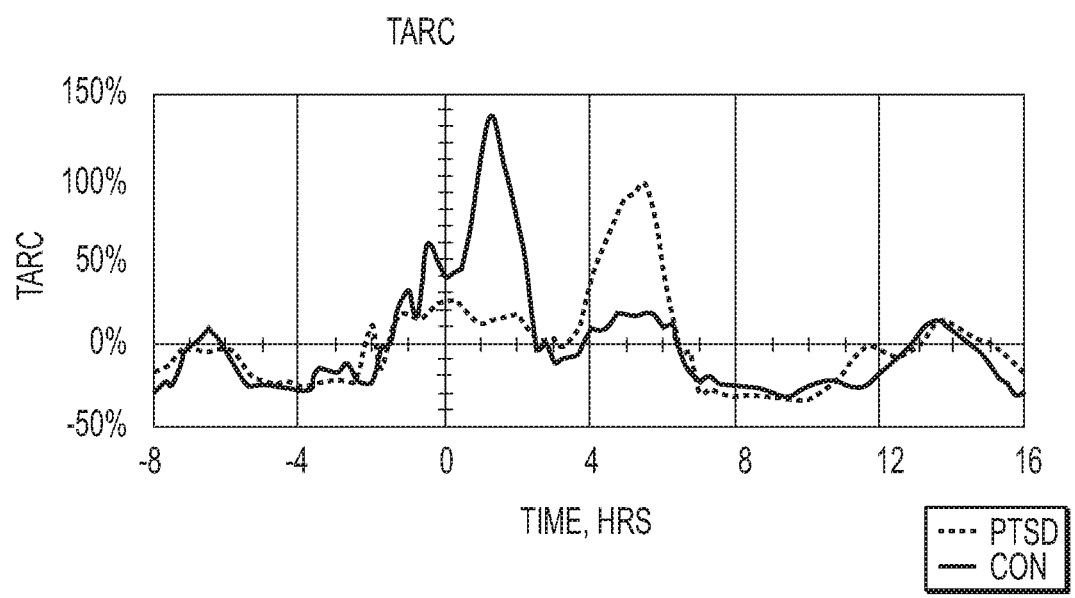
Figure 7F:
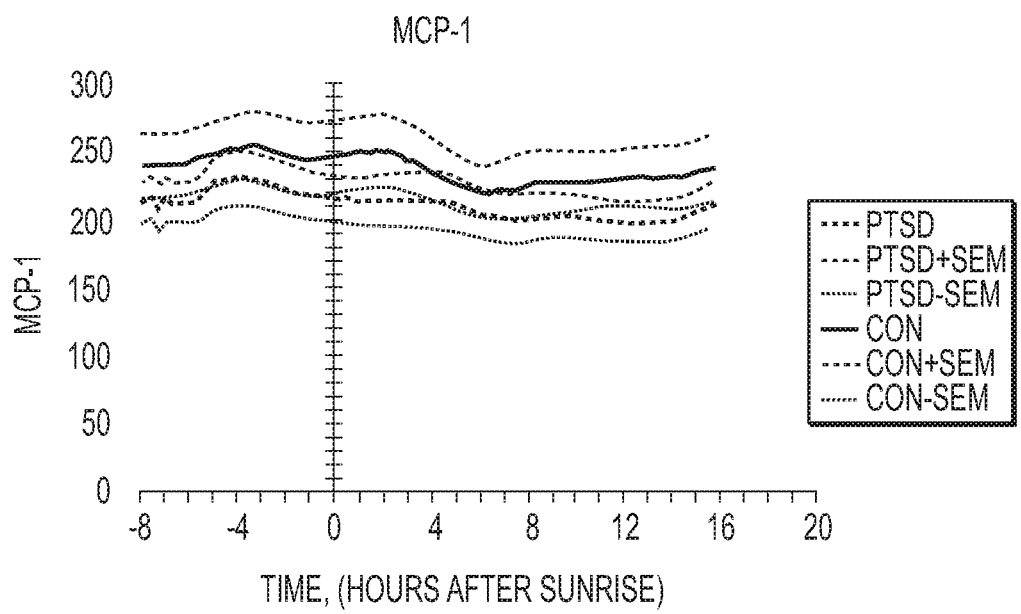
Figure 7F:
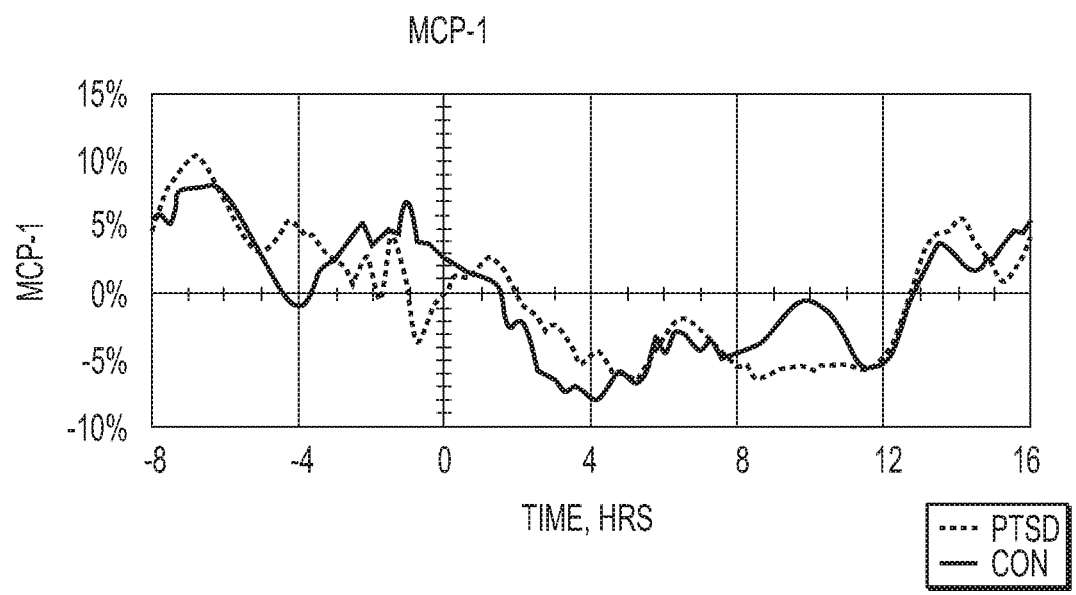
Figure 7G:
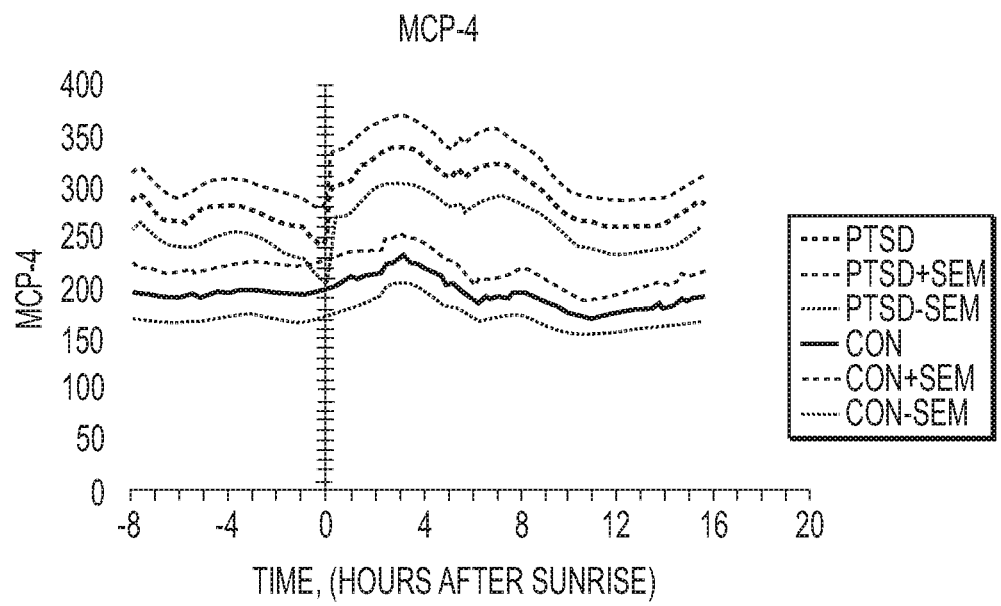
Figure 7G:
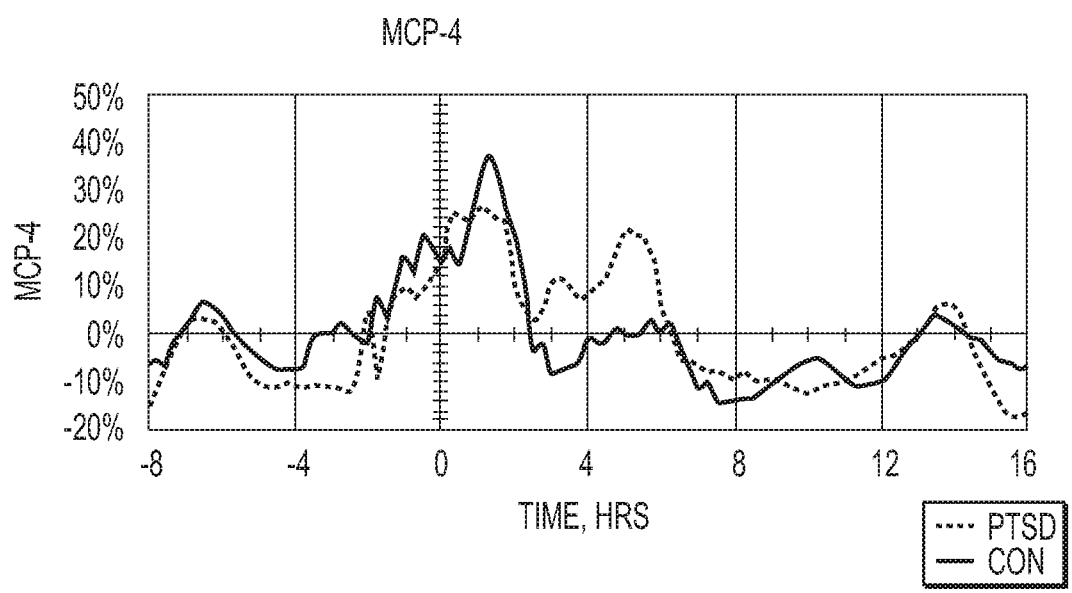
Figure 7H:
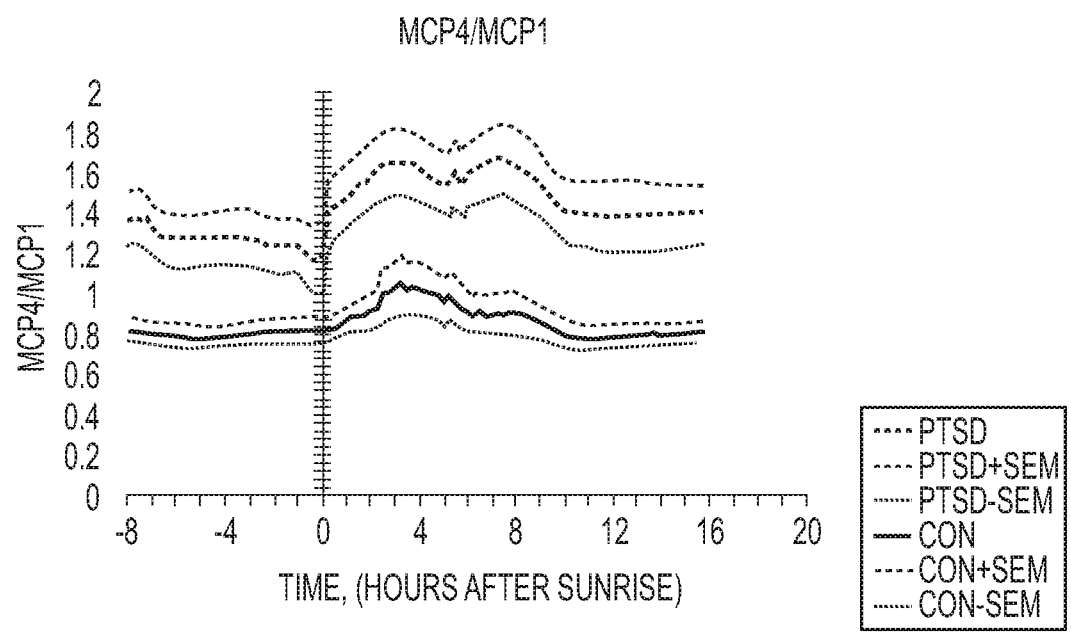
Figure 7H:
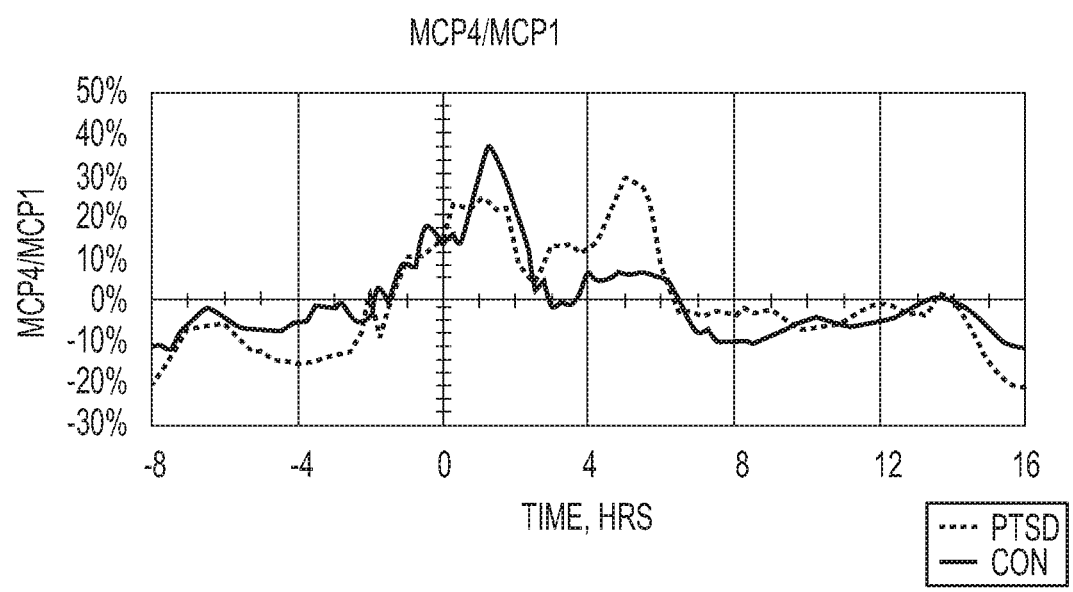

FIG. 4 also shows a difference plot for ([MCP-4]−[MCP-1]) from the 9 AM plasma samples. The statistical significance for the difference was the same as for the ratio (p=0.004).

FIG. 2a shows the 24 hour profile for the MCP-4/MCP-1 ratio in plasma from 5 PTSD and 5 healthy controls. The data indicate that across the entire 24 hour time period, the scale-free MCP-4/MCP-1 ratio for PTSD patients remained approximately twice that of healthy controls. Thus the ratio itself constitutes a viable metric that can be computed at any time a blood collection is made. Normalized and filtered data in FIG. 2b shows that the MCP4/MCP-1 ratio in healthy controls peaks once in the late night hours. The PTSD patients, on the other hand, have a two peaks, coinciding with the late night healthy control peak, and another occurring later in the morning.

FIG. 2c also shows that MCP-4 peaks four times throughout the day in PTSD patients, compared to only once in healthy controls. Furthermore, the late night MCP-4 peak in PTSD patients trails the peak times healthy control by almost three hours. Similar but unique temporal disorder appears to also characterize the MCP-1 profile. For example, FIG. 2d shows that there is a late night peak in MCP-1 concentration in PTSD patients and healthy controls, but the late night peak in PTSD patients trails by nearly six hours.

Figure 3:
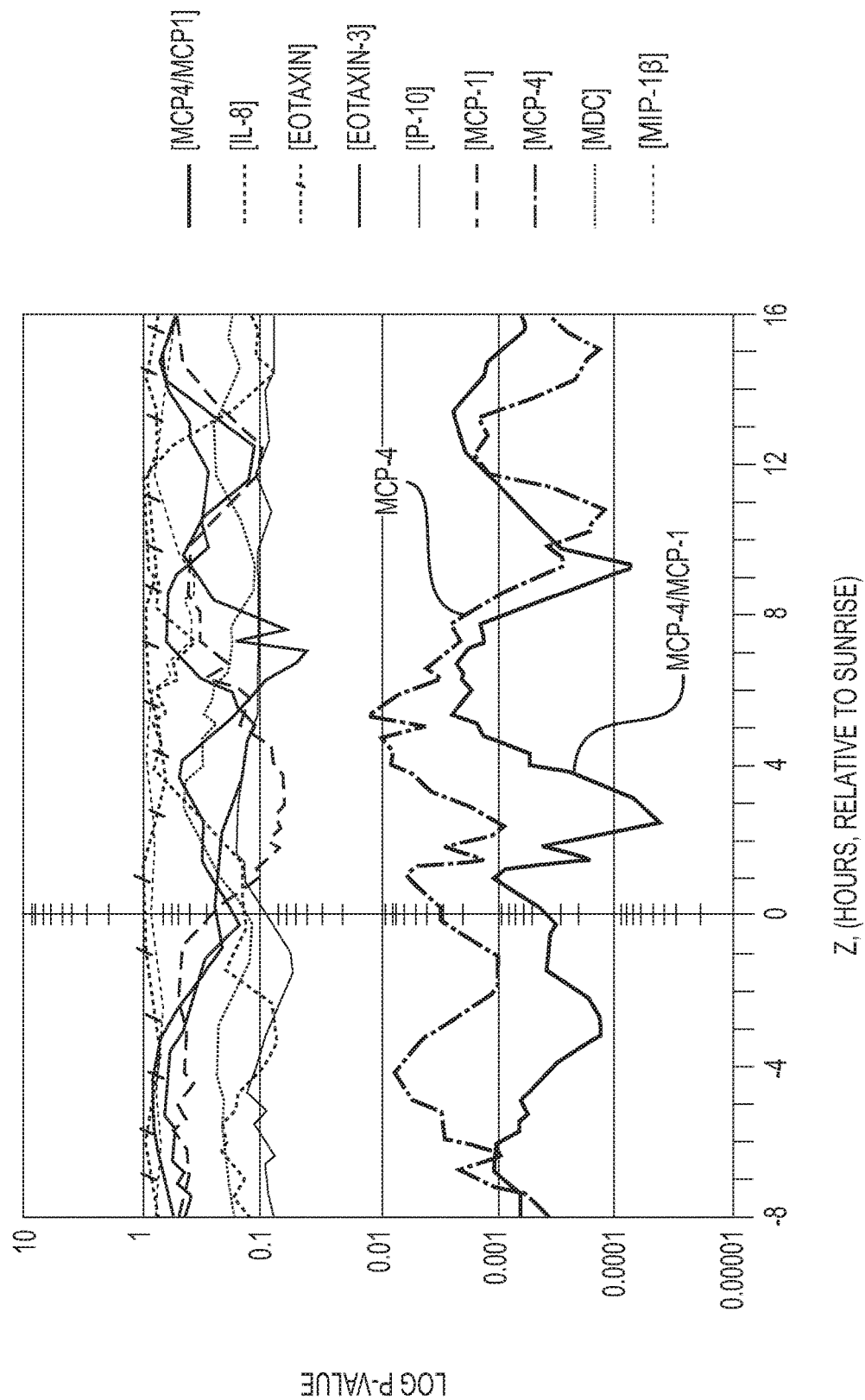
FIG. 3 depicts the tracking of MCP-4 and MCP-1 in healthy controls and PTSD patients. (a) healthy controls; (b) PTSD patients.

To further verify the specificity and significance of the MCP-4 and MCP-1 signals for PTSD, the circadian pattern of expression of seven other chemokines was tested for significance between PTSD patients and healthy controls across the entire 24 hour time period. Although there was an average difference between PTSD and healthy controls for some of these analytes, the variance among patients, shows substantial overlap in levels in all chemokines tested except for MCP-4. FIG. 3 plots the p-values for the hourly differences between PTSD and healthy controls for all chemokines tested, versus the MCP-4/MCP-1 ratio, across the circadian 24 hour time period. The P-values for, MCP-4 and the MCP-4/MCP-1 ratio are in the range of between p=0.01 to 0.0001. The best statistics for the MCP-4/MCP-1 ratio are at 3-4 hours past Z=0 (8-10 AM). In contrast to MCP-4, the other analytes were clustered individually in the statistical space occupied by p values between 0.1 and 1.0.

However, the noisy properties of individual circadian rhythm components is well known in the chronobiology literature. An alternative solution has been to compare differences in circadian rhythm for specific analytes by (i) filtering ("smoothing out") the variation from hour to hour by making a moving average of every three hours; (ii) averaging the results for 5 individuals; (iii) and ratio'ing all data to the mean for the entire 24 hour period [28]. Using these methods, FIG. 7(A-H) shows that for the different chemokines tested, the circadian rhythms are disordered for PTSD patients, although significant, quantitative, time-independent differences can only be detected for the MCP-4/MCP-1 ratio. It is indeed not typical that a ratio of two unrelated markers would be useful for identifying a subject having a specific disease or condition.

Figure 8B:
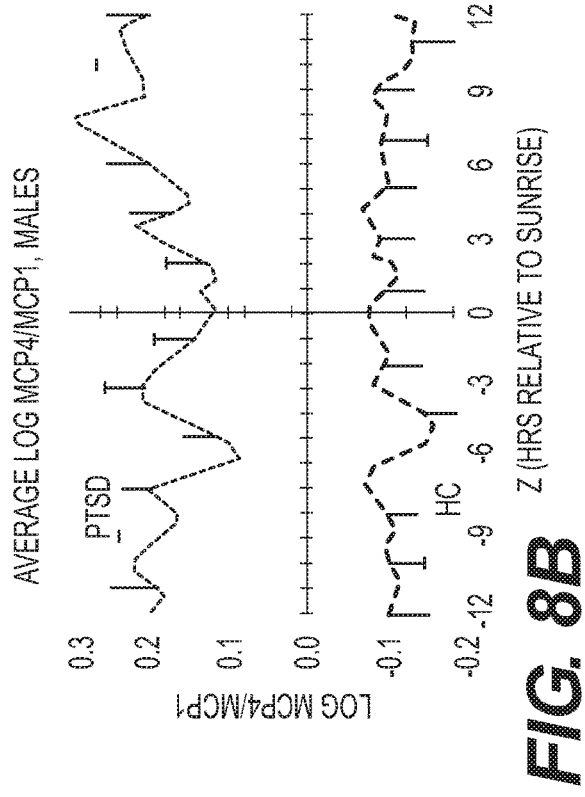
FIG. 8 (A-D) depicts the distribution of MCP-4/MCP-1 ratio in plasma over a circadian interval for patients with PTSD and healthy controls.
Figure 8D:
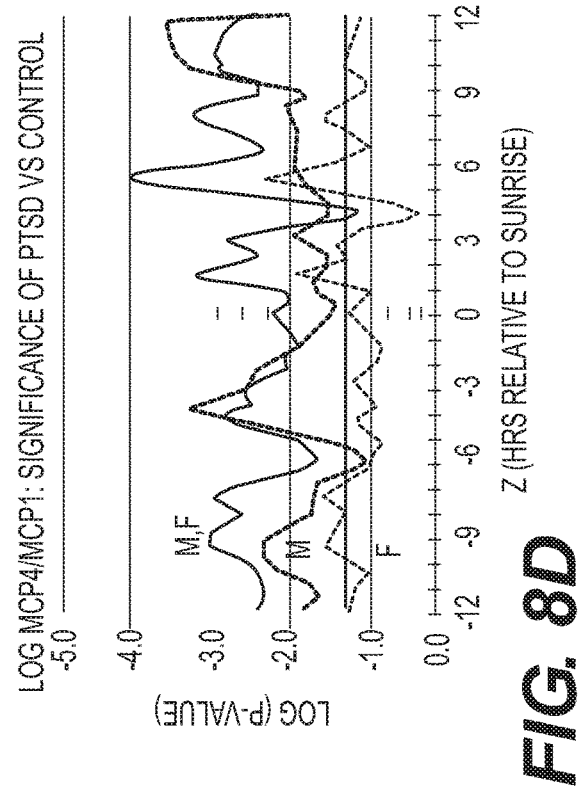
Figure 8A:
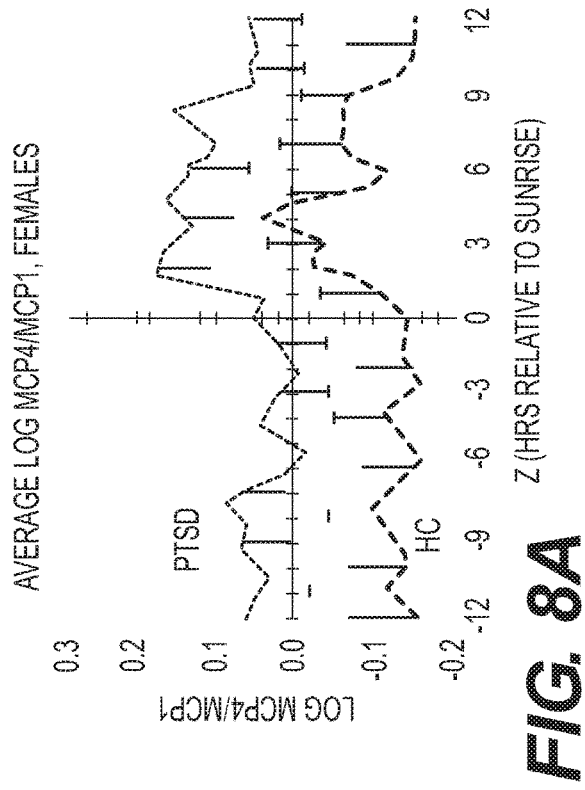
Figure 8C:
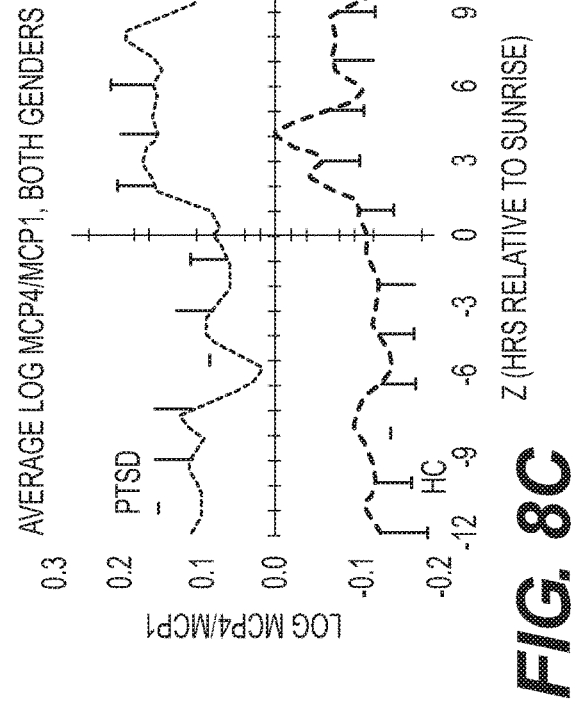

FIG. 8A shows the differences between average log plasma MCP-4/MCP-1 ratio in female PTSD patients vs female healthy controls. PTSD females are greater than healthy control females at every hour and the differences are significant, or trend to being significant at each hour (p<0.05), across circadian time. FIG. 8B shows the differences between average log plasma MCP-4/MCP-1 ratio in male PTSD patients vs male healthy controls. PTSD males are significantly greater than Healthy Control males at every hour (p<0.05). FIG. 8C shows the differences between average log plasma MCP-4/MCP-1 ratio in all PTSD patients vs all healthy controls. All PTSD patients are greater than all Healthy Controls at every hour and the differences are significant (p<0.05). P values for each of the differences (FIG. 8A-8C) at each hour are shown in FIG. 8D. Error bars are +/− SEM (standard error of the mean).

FIG. 9A shows the differences between average log plasma MIP-1β levels in female PTSD patients vs female healthy controls. PTSD Females are greater than Healthy Control females at every hour and the differences are significant, or trend to being significant at each hour across circadian time. (p<0.05). FIG. 9B shows the differences between average log plasma MIP-1β levels in male PTSD patients vs male healthy controls. PTSD males are trend slightly greater than Healthy Control males at every hour, but these differences at every hour are not significant across circadian time, (p<0.05). FIG. 9C shows the differences between average log plasma MIP-1β levels in all PTSD patients vs all healthy controls. All PTSD patients trend greater than all Healthy Controls at every hour. However, this trend is based on the contribution from female PTSD patients only. FIG. 9D shows the significance of log plasma concentration differences for MIP-1β over circadian time. Red horizontal line is the same as P=0.05 on a arithmetic scale. Male PTSD (dotted black line); female PTSD (dashed black line); all PTSD (solid black line). Vertical axis is log P value. Error bars are +/− SEM (standard error of the mean). P values for the difference at each hour are shown in FIG. 9D.

FIG. 10A shows the differences between average log plasma TARC levels in female PTSD patients vs female healthy controls. Differences between PTSD females and healthy control females at every hour are not significant (p<0.05). FIG. 10B shows the differences between average log plasma TARC levels in male PTSD patients are lower than male healthy controls. PTSD males are differ significantly at each hour across circadian time from healthy controls only at about Z-12 and Z, (p<0.05). FIG. 10C shows the differences between average log plasma TARC levels in all PTSD patients vs all healthy controls. There are no significant differences at each hour across circadian time, (p<0.05). FIG. 10D shows the significance of log plasma concentration differences for TARC lover circadian time. Red horizontal line is the same as P=0.05 on an arithmetic scale. Male PTSD (dotted black line); female PTSD (dashed black line); all PTSD (solid black line). Male PTSD patients differ significantly from male healthy controls at every hour across circadian time only at about Z-12 and Z, (p<0.05). Error bars are +/− SEM (standard error of the mean). P values for the difference at each hour are shown in FIG. 10D.

All references herein are incorporated by reference.

1. Bonne O, Gill J M, Luckenbaugh D A, Collins C, Owens M J, et al. (2011) Corticotropin-releasing factor, interleukin-6, brain-derived neurotrophic factor, insulin-like growth factor-1, and substance P in the cerebrospinal fluid of civilians with posttraumatic stress disorder before and after treatment with paroxetine. J Clin Psychiatry 72: 1124-1128.
2. Association A P (2013) Diagnostic and Statistical Manual of Mental disorders. Washington D.C.: American Psychiatric Publishing.
3. http://www.behavenet.com/capsules/disorders/ptsd.htm.
4. Boscarino J A (2004) Posttraumatic stress disorder and physical illness: results from clinical and epidemiologic studies. Ann N Y Acad Sci 1032: 141-153.
5. Gill J M, Saligan L, Woods S, Page G (2009) PTSD is associated with an excess of inflammatory immune activities. Perspect Psychiatr Care 45: 262-277.
6. Pace T W, Heim C M (2011) A short review on the psychoneuroimmunology of posttraumatic stress disorder: from risk factors to medical comorbidities. Brain Behav Immun 25: 6-13.
7. Daskalakis N P, Lehrner A, Yehuda R (2013) Endocrine aspects of post-traumatic stress disorder and implications for diagnosis and treatment. Endocrinol Metab Clin North Am 42: 503-513.
8. Elenkov I J, Iezzoni D G, Daly A, Harris A G, Chrousos G P (2005) Cytokine dysregulation, inflammation and well-being. Neuroimmunomodulation 12: 255-269.
9. Cunningham-Bussel A C, Root J C, Butler T, Tuescher O, Pan H, et al. (2009) Diurnal cortisol amplitude and fronto-limbic activity in response to stressful stimuli. Psychoneuroendocrinology 34: 694-704.
10. Raison C L, Miller A H (2003) When not enough is too much: the role of insufficient glucocorticoid signaling in the pathophysiology of stress-related disorders. Am J Psychiatry 160: 1554-1565.
11. Silverman M N, Pearce B D, Biron C A, Miller A H (2005) Immune modulation of the hypothalamic-pituitary-adrenal (HPA) axis during viral infection. Viral Immunol 18: 41-78.
12. Spivak B, Shohat B, Mester R, Avraham S, Gil-Ad I, et al. (1997) Elevated levels of serum interleukin-1 beta in combat-related posttraumatic stress disorder. Biol Psychiatry 42: 345-348.
13. von Kanel R, Hepp U, Kraemer B, Traber R, Keel M, et al. (2007) Evidence for low-grade systemic proinflammatory activity in patients with posttraumatic stress disorder. J Psychiatr Res 41: 744-752.
14. Maes M, Lin A H, Delmeire L, Van Gastel A, Kenis G, et al. (1999) Elevated serum interleukin-6 (IL-6) and IL-6 receptor concentrations in posttraumatic stress disorder following accidental man-made traumatic events. Biol Psychiatry 45: 833-839.
15. Tucker P, Jeon-Slaughter H, Pfefferbaum B, Khan Q, Davis N J (2010) Emotional and biological stress measures in Katrina survivors relocated to Oklahoma. Am J Disaster Med 5: 113-125.
16. Baker D G, Ekhator N N, Kasckow J W, Hill K K, Zoumakis E, et al. (2001) Plasma and cerebrospinal fluid interleukin-6 concentrations in posttraumatic stress disorder. Neuroimmunomodulation 9: 209-217.
17. Geracioti T D, Jr., Baker D G, Ekhator N N, West S A, Hill K K, et al. (2001) CSF norepinephrine concentrations in posttraumatic stress disorder. Am J Psychiatry 158: 1227-1230.
18. Hoge E A, Brandstetter K, Moshier S, Pollack M H, Wong K K, et al. (2009) Broad spectrum of cytokine abnormalities in panic disorder and posttraumatic stress disorder. Depress Anxiety 26: 447-455.
19. Baker D G, Nievergelt C M, O'Connor D T (2012) Biomarkers of PTSD: neuropeptides and immune signaling. Neuropharmacology 62: 663-673.
20. Gill J, Luckenbaugh D, Charney D, Vythilingam M (2010) Sustained elevation of serum interleukin-6 and relative insensitivity to hydrocortisone differentiates posttraumatic stress disorder with and without depression. Biol Psychiatry 68: 999-1006.
21. Ross R J, Ball W A, Sullivan K A, Caroff S N (1989) Sleep disturbance as the hallmark of posttraumatic stress disorder. Am J Psychiatry 146: 697-707.
22. Harvey A G, Jones C, Schmidt D A (2003) Sleep and posttraumatic stress disorder: a review. Clin Psychol Rev 23: 377-407.
23. Pollard J R, Eidelman O, Mueller G P, Dalgard C L, Crino P B, et al. (2012) The TARC/sICAM5 Ratio in Patient Plasma is a Candidate Biomarker for Drug Resistant Epilepsy. Front Neurol 3: 181.
24. Westin K, Buchhave P, Nielsen H, Minthon L, Janciauskiene S, et al. (2012) CCL2 is associated with a faster rate of cognitive decline during early stages of Alzheimer's disease. PLoS One 7: e30525.
25. Wild E, Magnusson A, Lahiri N, Krus U, Orth M, et al. (2011) Abnormal peripheral chemokine profile in Huntington's disease. PLoS Curr 3: Rrn1231.

26. Janelidze S, Ventorp F, Erhardt S, Hansson O, Minthon L, et al. (2013) Altered chemokine levels in the cerebrospinal fluid and plasma of suicide attempters. Psychoneuroendocrinology 38: 853-862.
27. Irwin D J, McMillan C T, Toledo J B, Arnold S E, Shaw L M, et al. (2012) Comparison of cerebrospinal fluid levels of tau and Abeta 1-42 in Alzheimer disease and frontotemporal degeneration using 2 analytical platforms. Arch Neurol 69: 1018-1025.
28. Eckel-Mahan K L, Patel V R, de Mateo S, Orozco-Solis R, Ceglia N J, et al. (2013) Reprogramming of the circadian clock by nutritional challenge. Cell 155: 1464-1478.
29. Garcia-Zepeda E A, Combadiere C, Rothenberg M E, Sarafi M N, Lavigne F, et al. (1996) Human monocyte chemoattractant protein (MCP)-4 is a novel C C chemokine with activities on monocytes, eosinophils, and basophils induced in allergic and nonallergic inflammation that signals through the C C chemokine receptors (CCR)-2 and -3. J Immunol 157: 5613-5626.
30. Blanpain C, Migeotte I, Lee B, Vakili J, Doranz B J, et al. (1999) CCR5 binds multiple C C-chemokines: MCP-3 acts as a natural antagonist. Blood 94: 1899-1905.
31. Segman R H, Shefi N, Goltser-Dubner T, Friedman N, Kaminski N, et al. (2005) Peripheral blood mononuclear cell gene expression profiles identify emergent posttraumatic stress disorder among trauma survivors. Mol Psychiatry 10: 500-513, 425.
32. Yehuda R, Cai G, Golier J A, Sarapas C, Galea S, et al. (2009) Gene expression patterns associated with posttraumatic stress disorder following exposure to the World Trade Center attacks. Biol Psychiatry 66: 708-711.
33. Neylan T C, Sun B, Rempel H, Ross J, Lenoci M, et al. (2011) Suppressed monocyte gene expression profile in men versus women with PTSD. Brain Behav Immun 25: 524-531.
34. Nguyen K D, Fentress S J, Qiu Y, Yun K, Cox J S, et al. (2013) Circadian gene Bmal1 regulates diurnal oscillations of Ly6C(hi) inflammatory monocytes. Science 341: 1483-1488.
35. Druzd D, Scheiermann C (2013) Immunology. Some monocytes got rhythm. Science 341: 1462-1464.
36. Born J, Lange T, Hansen K, Molle M, Fehm H L (1997) Effects of sleep and circadian rhythm on human circulating immune cells. J Immunol 158: 4454-4464.
37. Grimaldi B, Nakahata Y, Sahar S, Kaluzova M, Gauthier D, et al. (2007) Chromatin remodeling and circadian control: master regulator CLOCK is an enzyme. Cold Spring Harb Symp Quant Biol 72: 105-112.
38. Menet J S, Rosbash M (2011) When brain clocks lose track of time: cause or consequence of neuropsychiatric disorders. Curr Opin Neurobiol 21: 849-857.

What is claimed is:

1. A method of detecting one or more proteins in a male human subject suspected to have a post-traumatic stress disorder (PTSD), the method comprising:
    obtaining a biological plasma sample from the male human subject suspected to have the PTSD;
    measuring a level of monocyte chemoattractant protein 1 (MCP-1) having an amino acid sequence of SEQ ID NO: 1 or SEQ ID NO: 2, and thymus activation-regulated chemokine (TARC) having an amino acid sequence of SEQ ID NO: 3 or SEQ ID NO: 4 in the biological plasma sample;
    determining a normal level of the MCP-1 and TARC, wherein the normal level of the MCP-1 and TARC is determined from at least one biological sample previously obtained from the male human subject or from biological samples obtained from a population of male individuals that do not suffer from PTSD;
    determining a difference between the measured level of the MCP-1 and TARC and the normal level of MCP-1 and TARC,
    wherein a decrease in the level of the MCP-1 and TARC compared to the normal level of the MCP-1 and TARC indicates that the male human subject has an increased risk of suffering from PTSD; and
    administering at least one selective serotonin reuptake inhibitor (SSRI) to the male human subject when the decrease in the level of the MCP-1 and TARC compared to the normal level of the MCP-1 and TARC is determined, wherein the SSRI is selected from the group consisting of citalopram, dapoxetine, escitalopram, fluoxetine, fluvoxamine, indalpine, paroxetine, sertraline and zimelidine.

2. The method of claim 1, wherein the biological plasma sample is collected at one or more time points.

3. The method of claim 1, wherein the biological plasma sample is collected at about 2:00 a.m. (0200 hours) and/or at about 9:00 a.m (0900 hours).

4. The method of claim 1, wherein the human subject was diagnosed with a depressive disorder prior to determining the level of the MCP-1 and TARC.

5. The method of claim 4, wherein the human subject was treated for a depressive disorder prior to determining the level of the MCP-1 and TARC.

6. The method of claim 1, wherein the at least one the biological sample obtained from the male human subject is obtained from the male human subject prior to a suspected onset of the PTSD in the male human subject.

7. The method of claim 6, wherein the PTSD is a measurable, perceivable, or diagnosed PTSD.

* * * * *

SEQUENCE LISTING

```
<160> NUMBER OF SEQ ID NOS: 11

<210> SEQ ID NO 1
<211> LENGTH: 99
<212> TYPE: PRT
<213> ORGANISM: Homo sapiens

<400> SEQUENCE: 1

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr

<210> SEQ ID NO 2
<211> LENGTH: 76
<212> TYPE: PRT
<213> ORGANISM: Homo sapiens

<400> SEQUENCE: 2

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45
```

```
Lys Glu Ile Cys Ala Asp Pro Lys Gln Lys Trp Val Gln Asp Ser Met
 50                  55                  60

Asp His Leu Asp Lys Gln Thr Gln Thr Pro Lys Thr
 65                  70                  75
```

<210> SEQ ID NO 3
<211> LENGTH: 94
<212> TYPE: PRT
<213> ORGANISM: Homo sapiens

<400> SEQUENCE: 3

```
Met Ala Pro Leu Lys Met Leu Ala Leu Val Thr Leu Leu Leu Gly Ala
 1               5                  10                  15

Ser Leu Gln His Ile His Ala Ala Arg Gly Thr Asn Val Gly Arg Glu
                 20                  25                  30

Cys Cys Leu Glu Tyr Phe Lys Gly Ala Ile Pro Leu Arg Lys Leu Lys
             35                  40                  45

Thr Trp Tyr Gln Thr Ser Glu Asp Cys Ser Arg Asp Ala Ile Val Phe
 50                  55                  60

Val Thr Val Gln Gly Arg Ala Ile Cys Ser Asp Pro Asn Asn Lys Arg
 65                  70                  75                  80

Val Lys Asn Ala Val Lys Tyr Leu Gln Ser Leu Glu Arg Ser
                 85                  90
```

<210> SEQ ID NO 4
<211> LENGTH: 71
<212> TYPE: PRT
<213> ORGANISM: Homo sapiens

<400> SEQUENCE: 4

```
Ala Arg Gly Thr Asn Val Gly Arg Glu Cys Cys Leu Glu Tyr Phe Lys
 1               5                  10                  15

Gly Ala Ile Pro Leu Arg Lys Leu Lys Thr Trp Tyr Gln Thr Ser Glu
                 20                  25                  30

Asp Cys Ser Arg Asp Ala Ile Val Phe Val Thr Val Gln Gly Arg Ala
             35                  40                  45

Ile Cys Ser Asp Pro Asn Asn Lys Arg Val Lys Asn Ala Val Lys Tyr
 50                  55                  60

Leu Gln Ser Leu Glu Arg Ser
 65                  70
```

<210> SEQ ID NO 5
<211> LENGTH: 92
<212> TYPE: PRT
<213> ORGANISM: Homo sapiens

<400> SEQUENCE: 5

```
Met Lys Leu Cys Val Thr Val Leu Ser Leu Leu Met Leu Val Ala Ala
 1               5                  10                  15

Phe Cys Ser Pro Ala Leu Ser Ala Pro Met Gly Ser Asp Pro Pro Thr
                 20                  25                  30

Ala Cys Cys Phe Ser Tyr Thr Ala Arg Lys Leu Pro Arg Asn Phe Val
             35                  40                  45

Val Asp Tyr Tyr Glu Thr Ser Ser Leu Cys Ser Gln Pro Ala Val Val
 50                  55                  60

Phe Gln Thr Lys Arg Ser Lys Gln Val Cys Ala Asp Pro Ser Glu Ser
 65                  70                  75                  80
```

Trp Val Gln Glu Tyr Val Tyr Asp Leu Glu Leu Asn
                85                  90

<210> SEQ ID NO 6
<211> LENGTH: 69
<212> TYPE: PRT
<213> ORGANISM: Homo sapiens

<400> SEQUENCE: 6

Ala Pro Met Gly Ser Asp Pro Pro Thr Ala Cys Cys Phe Ser Tyr Thr
1               5                   10                  15

Ala Arg Lys Leu Pro Arg Asn Phe Val Val Asp Tyr Tyr Glu Thr Ser
                20                  25                  30

Ser Leu Cys Ser Gln Pro Ala Val Val Phe Gln Thr Lys Arg Ser Lys
            35                  40                  45

Gln Val Cys Ala Asp Pro Ser Glu Ser Trp Val Gln Glu Tyr Val Tyr
        50                  55                  60

Asp Leu Glu Leu Asn
65

<210> SEQ ID NO 7
<211> LENGTH: 67
<212> TYPE: PRT
<213> ORGANISM: Homo sapiens

<400> SEQUENCE: 7

Met Gly Ser Asp Pro Pro Thr Ala Cys Cys Phe Ser Tyr Thr Ala Arg
1               5                   10                  15

Lys Leu Pro Arg Asn Phe Val Val Asp Tyr Tyr Glu Thr Ser Ser Leu
                20                  25                  30

Cys Ser Gln Pro Ala Val Val Phe Gln Thr Lys Arg Ser Lys Gln Val
            35                  40                  45

Cys Ala Asp Pro Ser Glu Ser Trp Val Gln Glu Tyr Val Tyr Asp Leu
        50                  55                  60

Glu Leu Asn
65

<210> SEQ ID NO 8
<211> LENGTH: 98
<212> TYPE: PRT
<213> ORGANISM: Homo sapiens

<400> SEQUENCE: 8

Met Lys Val Ser Ala Val Leu Leu Cys Leu Leu Met Thr Ala Ala
1               5                   10                  15

Phe Asn Pro Gln Gly Leu Ala Gln Pro Asp Ala Leu Asn Val Pro Ser
                20                  25                  30

Thr Cys Cys Phe Thr Phe Ser Ser Lys Lys Ile Ser Leu Gln Arg Leu
            35                  40                  45

Lys Ser Tyr Val Ile Thr Thr Ser Arg Cys Pro Gln Lys Ala Val Ile
        50                  55                  60

Phe Arg Thr Lys Leu Gly Lys Glu Ile Cys Ala Asp Pro Lys Glu Lys
65                  70                  75                  80

Trp Val Gln Asn Tyr Met Lys His Leu Gly Arg Lys Ala His Thr Leu
                85                  90                  95

Lys Thr

<210> SEQ ID NO 9

```
<211> LENGTH: 82
<212> TYPE: PRT
<213> ORGANISM: Homo sapiens

<400> SEQUENCE: 9

Phe Asn Pro Gln Gly Leu Ala Gln Pro Asp Ala Leu Asn Val Pro Ser
1               5                   10                  15

Thr Cys Cys Phe Thr Phe Ser Ser Lys Lys Ile Ser Leu Gln Arg Leu
            20                  25                  30

Lys Ser Tyr Val Ile Thr Thr Ser Arg Cys Pro Gln Lys Ala Val Ile
        35                  40                  45

Phe Arg Thr Lys Leu Gly Lys Glu Ile Cys Ala Asp Pro Lys Glu Lys
    50                  55                  60

Trp Val Gln Asn Tyr Met Lys His Leu Gly Arg Lys Ala His Thr Leu
65                  70                  75                  80

Lys Thr

<210> SEQ ID NO 10
<211> LENGTH: 77
<212> TYPE: PRT
<213> ORGANISM: Homo sapiens

<400> SEQUENCE: 10

Leu Ala Gln Pro Asp Ala Leu Asn Val Pro Ser Thr Cys Cys Phe Thr
1               5                   10                  15

Phe Ser Ser Lys Lys Ile Ser Leu Gln Arg Leu Lys Ser Tyr Val Ile
            20                  25                  30

Thr Thr Ser Arg Cys Pro Gln Lys Ala Val Ile Phe Arg Thr Lys Leu
        35                  40                  45

Gly Lys Glu Ile Cys Ala Asp Pro Lys Glu Lys Trp Val Gln Asn Tyr
    50                  55                  60

Met Lys His Leu Gly Arg Lys Ala His Thr Leu Lys Thr
65                  70                  75

<210> SEQ ID NO 11
<211> LENGTH: 75
<212> TYPE: PRT
<213> ORGANISM: Homo sapiens

<400> SEQUENCE: 11

Gln Pro Asp Ala Leu Asn Val Pro Ser Thr Cys Cys Phe Thr Phe Ser
1               5                   10                  15

Ser Lys Lys Ile Ser Leu Gln Arg Leu Lys Ser Tyr Val Ile Thr Thr
            20                  25                  30

Ser Arg Cys Pro Gln Lys Ala Val Ile Phe Arg Thr Lys Leu Gly Lys
        35                  40                  45

Glu Ile Cys Ala Asp Pro Lys Glu Lys Trp Val Gln Asn Tyr Met Lys
    50                  55                  60

His Leu Gly Arg Lys Ala His Thr Leu Lys Thr
65                  70                  75
```